(12) United States Patent
Tally et al.

(10) Patent No.: US 6,436,694 B1
(45) Date of Patent: Aug. 20, 2002

(54) REGULABLE GENE EXPRESSION IN GRAM-POSITIVE BACTERIA

(75) Inventors: Francis P. Tally, Lincoln; Jianshi Tao, North Andover; Xiaoyu Shen, Boston; Jiansu Zhang, Roslindale, all of MA (US)

(73) Assignee: Cubist Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 09/291,874

(22) Filed: Apr. 14, 1999

Related U.S. Application Data

(63) Continuation-in-part of application No. 09/227,687, filed on Jan. 8, 1999.
(60) Provisional application No. 60/070,965, filed on Jan. 9, 1998, provisional application No. 60/076,638, filed on Mar. 3, 1998, provisional application No. 60/081,753, filed on Apr. 14, 1998, provisional application No. 60/085,844, filed on May 18, 1998, provisional application No. 60/089,828, filed on Jun. 19, 1998, provisional application No. 60/094,698, filed on Jul. 30, 1998, provisional application No. 60/100,211, filed on Sep. 14, 1998, provisional application No. 60/101,718, filed on Sep. 24, 1998, provisional application No. 60/107,751, filed on Nov. 10, 1998, and provisional application No. 60/122,949, filed on Mar. 5, 1999.

(51) Int. Cl.$^7$ .............................. C12N 1/00; C12N 1/20; C12P 1/06; C12Q 1/68; C07H 21/04
(52) U.S. Cl. .................. 435/252.3; 435/69.1; 435/69.7; 435/243; 435/6; 435/320.1; 435/91.4; 536/23.1; 536/23.4; 536/24.1
(58) Field of Search .............. 435/320.1, 69.1, 435/252.3, 243, 6, 91.4, 69.7; 536/23.1, 23.4, 24.1

(56) References Cited

U.S. PATENT DOCUMENTS

| | | | |
|---|---|---|---|
| 5,789,188 A | * | 8/1998 | Rothstein et al. ............. 435/29 |
| 5,849,576 A | | 12/1998 | Skerra et al. ............. 435/320.1 |

FOREIGN PATENT DOCUMENTS

| | | |
|---|---|---|
| DE | 3934454 A | 4/1991 |
| WO | WO 91/00913 | 1/1991 |
| WO | WO 98/10079 | 3/1998 |
| WO | WO 99/36554 | 7/1999 |

OTHER PUBLICATIONS

The 1995 Pharmacia Catalog, pp. 198–199, 1995.*
Geissendörfer, M. and Hillen, W., "Regulated expression of heterologous genes in *Bacillus subtilis* using the Tn10 encoded tet regulatory elements," *Appl. Microbiol. Biotechnol.* 33(6) : 657–663 (1990).
Eichenbaum, Z. et al., "Use of the Lactococcal nisA Promoter To Regulate Gene Expression in Gram–Positive Bacteria: Comparison of Induction Level and Promoter Strength," *Appl. Environ. Microbiol.*, 64 (8) :2763–2769 (1998).
Gärtner, D. et al., "Expression of the *Bacillus subtilis* xyl Operon Is Repressed at the Level of Transcription and Is Induced by Xylose," *J. Bacteriol.* 170 (7) :3102–3109 (1988).
Wieland, K.P. et al., "A promoter–screening plasmid and xylose–inducible, glucose–repressible expression victor for *Staphylococcus carnosus*," *Gene* 158:91–96 (1995).
de Vos, W.M. et al., "Expression systems for Industrial Gram–positive bacteria with low guanine and cytosine content," *Current Opinion in Biotechnology* 8:547–553 (1997).
Skerra, A., "Use of the tetracycline promoter for the tightly regulated production of a murine antibody fragment in *Escherichia coli*," *Gene* 151:131–135 (1994).

* cited by examiner

Primary Examiner—David Guzo
Assistant Examiner—Gerald G. Leffers, Jr.
(74) Attorney, Agent, or Firm—Hamilton, Brook, Smith & Reynolds, P.C.

(57) ABSTRACT

A system has been constructed which is suitable for tetracycline-inducible gene expression in Gram-positive bacteria such as *Staphylococcus aureus* and *Bacillus subtilis*. The replicon/host gene expression system is tightly regulated, can be used in complex as well as minimal media, and can produce a high level of gene expression upon induction, with a variety of gene products. The gene expression system is suitable for production of products toxic to the host cells, and can be used, for example, for the analysis of gene expression and gene products in Gram-positive bacteria, and in a test of the effect of a peptide or polypeptide inhibitor of an *S. aureus* enzyme on the growth of *S. aureus* cells in culture or during infection of an animal.

31 Claims, 12 Drawing Sheets

```
                          SEQUENCE LISTING

<160> NUMBER OF SEQ ID NOS: 28

<210> SEQ ID NO 1
<211> LENGTH: 33
<212> TYPE: DNA
<213> ORGANISM: Artificial Sequence
<220> FEATURE:
<223> OTHER INFORMATION: Oligonucleotide

<400> SEQUENCE: 1
acgggtcgac tcatatcttt tattcaataa tcg                                33

<210> SEQ ID NO 2
<211> LENGTH: 32
<212> TYPE: DNA
<213> ORGANISM: Artificial Sequence
<220> FEATURE:
<223> OTHER INFORMATION: Oligonucleotide

<400> SEQUENCE: 2
ccggaaagct tacttattaa ataatttata gc                                 32

<210> SEQ ID NO 3
<211> LENGTH: 34
<212> TYPE: DNA
<213> ORGANISM: Artificial Sequence
<220> FEATURE:
<223> OTHER INFORMATION: Oligonucleotide

<400> SEQUENCE: 3
taagtaagct taaggaggaa ttaatgatgt ctag                               34

<210> SEQ ID NO 4
<211> LENGTH: 34
<212> TYPE: DNA
<213> ORGANISM: Artificial Sequence
<220> FEATURE:
<223> OTHER INFORMATION: Oligonucleotide

<400> SEQUENCE: 4
acgggtcgac ttaagaccca ctttcacatt taag                               34

<210> SEQ ID NO 5
<211> LENGTH: 45
<212> TYPE: DNA
<213> ORGANISM: Artificial Sequence
<220> FEATURE:
<223> OTHER INFORMATION: Oligonucleotide

<400> SEQUENCE: 5
ctcggtaccg agctaaaatt cggaggcata tcaaatgagc tctgg                   45

<210> SEQ ID NO 6
<211> LENGTH: 44
<212> TYPE: DNA
<213> ORGANISM: Artificial Sequence
<220> FEATURE:
<223> OTHER INFORMATION: Oligonucleotide

<400> SEQUENCE: 6
```

-continued ggcatatcaa atgagctctg gaggtggagg catgtcccct atac          44

<210> SEQ ID NO 7
<211> LENGTH: 31
<212> TYPE: DNA
<213> ORGANISM: Artificial Sequence
<220> FEATURE:
<223> OTHER INFORMATION: Oligonucleotide

<400> SEQUENCE: 7
aggcctaggt taatccgatt ttggaggatg g          31

<210> SEQ ID NO 8
<211> LENGTH: 42
<212> TYPE: DNA
<213> ORGANISM: Artificial Sequence
<220> FEATURE:
<223> OTHER INFORMATION: Oligonucleotide

<400> SEQUENCE: 8
ctgatccgaa tacgtggcag ttgcggtggc ctatgcatag ct          42

<210> SEQ ID NO 9
<211> LENGTH: 42
<212> TYPE: DNA
<213> ORGANISM: Artificial Sequence
<220> FEATURE:
<223> OTHER INFORMATION: Oligonucleotide

<400> SEQUENCE: 9
atgcataggc caccgcaact gccacgtatt cggatcagag ct          42

<210> SEQ ID NO 10
<211> LENGTH: 48
<212> TYPE: DNA
<213> ORGANISM: Artificial Sequence
<220> FEATURE:
<223> OTHER INFORMATION: Oligonucleotide

<400> SEQUENCE: 10
tcgagttcat gaaaaactaa aaaaaatatt gacatcccta tcagtgat          48

<210> SEQ ID NO 11
<211> LENGTH: 45
<212> TYPE: DNA
<213> ORGANISM: Artificial Sequence
<220> FEATURE:
<223> OTHER INFORMATION: Oligonucleotide

<400> SEQUENCE: 11
agagataatt aaaataatcc ctatcagtga tagagagctt gcatg          45

<210> SEQ ID NO 12
<211> LENGTH: 29
<212> TYPE: DNA
<213> ORGANISM: Artificial Sequence
<220> FEATURE:
<223> OTHER INFORMATION: Oligonucleotide

<400> SEQUENCE: 12
caagctctct atcactgata gggattatt          29

<210> SEQ ID NO 13
<211> LENGTH: 56
<212> TYPE: DNA
<213> ORGANISM: Artificial Sequence

```
<220> FEATURE:
<223> OTHER INFORMATION: Oligonucleotide

<400> SEQUENCE: 13
ttaattatct ctatcactga tagggatgtc aatattttttt ttagtttttc atgaac        56

<210> SEQ ID NO 14
<211> LENGTH: 58
<212> TYPE: DNA
<213> ORGANISM: Artificial Sequence
<220> FEATURE:
<223> OTHER INFORMATION: Oligonucleotide

<400> SEQUENCE: 14
aataaaaaac tagtttgaca ataactcta tcaatgatag agtgtcacaa aaaggagg       58

<210> SEQ ID NO 15
<211> LENGTH: 56
<212> TYPE: DNA
<213> ORGANISM: Artificial Sequence
<220> FEATURE:
<223> OTHER INFORMATION: Oligonucleotide

<400> SEQUENCE: 15
gatagagtgt caacaaaaag gaggaattaa tgatgtcccc tatactaggt tattgg        56

<210> SEQ ID NO 16
<211> LENGTH: 36
<212> TYPE: DNA
<213> ORGANISM: Artificial Sequence
<220> FEATURE:
<223> OTHER INFORMATION: Oligonucleotide

<400> SEQUENCE: 16
ggattaaggt aaccttaatc cgattttgga ggatgg                              36

<210> SEQ ID NO 17
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 17

Asp Pro Asn Thr Trp Gln Leu Arg Trp Pro Met His
 1               5                  10

<210> SEQ ID NO 18
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 18

Gly Gly Arg Gly Gly Met
 1               5

<210> SEQ ID NO 19
<211> LENGTH: 54
<212> TYPE: DNA
<213> ORGANISM: Artificial Sequence
<220> FEATURE:
<223> OTHER INFORMATION: Oligonucleotide

<400> SEQUENCE: 19
```

-continued gatcctaata catggcagtt gaggtggcct atgcatggcg gccgcggagg tatg        54

<210> SEQ ID NO 20
<211> LENGTH: 66
<212> TYPE: DNA
<213> ORGANISM: Artificial Sequence
<220> FEATURE:
<223> OTHER INFORMATION: Oligonucleotide

<400> SEQUENCE: 20
agctctgatc ctaatacatg gcagttgagg tggcctatgc attcttcagg cggccgcgga   60
ggtatg                                                              66

<210> SEQ ID NO 21
<211> LENGTH: 21
<212> TYPE: PRT
<213> ORGANISM: Artificial Sequence
<220> FEATURE:
<223> OTHER INFORMATION: peptide

<400> SEQUENCE: 21

Ser Arg Trp Glu Lys Tyr Ile Asn Ser Phe Glu Leu Asp Ser Arg Gly
 1               5                  10                  15

Gly Arg Gly Gly Met
            20

<210> SEQ ID NO 22
<211> LENGTH: 63
<212> TYPE: DNA
<213> ORGANISM: Artificial Sequence
<220> FEATURE:
<223> OTHER INFORMATION: Oligonucleotide

<400> SEQUENCE: 22
tctagatggg aaaaatatat taattctttt gaattagatt ctcgaggtgg tagaggtgga   60
atg                                                                 63

<210> SEQ ID NO 23
<211> LENGTH: 21
<212> TYPE: PRT
<213> ORGANISM: Artificial Sequence
<220> FEATURE:
<223> OTHER INFORMATION: peptide

<400> SEQUENCE: 23

Ser Ser Gln Gly Thr Met Arg Trp Phe Asp Trp Tyr Arg Ser Arg Gly
 1               5                  10                  15

Gly Arg Gly Gly Met
            20

<210> SEQ ID NO 24
<211> LENGTH: 63
<212> TYPE: DNA
<213> ORGANISM: Artificial Sequence
<220> FEATURE:
<223> OTHER INFORMATION: Oligonucleotide

<400> SEQUENCE: 24
agctctcaag gtactatgag atggtttgat tggtatagat ctcgaggtgg tagaggtgga   60
atg                                                                 63

<210> SEQ ID NO 25
<211> LENGTH: 49

```
<212> TYPE: DNA
<213> ORGANISM: Artificial Sequence
<220> FEATURE:
<223> OTHER INFORMATION: Oligonucleotide

<400> SEQUENCE: 25
agcaccttgg cggccgcgga ggtgctagca aaggagaaga actcttcac          49

<210> SEQ ID NO 26
<211> LENGTH: 37
<212> TYPE: DNA
<213> ORGANISM: Artificial Sequence
<220> FEATURE:
<223> OTHER INFORMATION: Oligonucleotide

<400> SEQUENCE: 26
aactgaggta acctcagttg tacagttcat ccatgcc                       37

<210> SEQ ID NO 27
<211> LENGTH: 52
<212> TYPE: DNA
<213> ORGANISM: Artificial Sequence
<220> FEATURE:
<223> OTHER INFORMATION: Oligonucleotide

<400> SEQUENCE: 27
tttaccttgg cggccgcgga ggtaaactga agaaggtaaa ctggtaatct gg       52

<210> SEQ ID NO 28
<211> LENGTH: 40
<212> TYPE: DNA
<213> ORGANISM: Artificial Sequence
<220> FEATURE:
<223> OTHER INFORMATION: Oligonucleotide

<400> SEQUENCE: 28
acttagggta accttaagtc tgcgcgtctt tcagggcttc                    40
```

REGULABLE GENE EXPRESSION IN GRAM-POSITIVE BACTERIA

RELATED APPLICATIONS

This application is a continuation-in-part of U.S. patent application Ser. No. 09/227,687 filed on Jan. 8, 1999, which claims the benefit of U.S. Provisional Application No. 60/070,965 filed on Jan. 9, 1998; U.S. Provisional Application No. 60/076,638 filed on Mar. 3, 1998; U.S. Provisional Application No. 60/081,753 filed on Apr. 14, 1998; U.S. Provisional Application No. 60/085,844 filed on May 18, 1998; U.S. Provisional Application No. 60/089,828 filed on Jun. 19, 1998; U.S. Provisional Application No. 60/094,698 filed on Jul. 30, 1998; U.S. Provisional Application No. 60/100,211 filed on Sep. 14, 1998; U.S. Provisional Application No. 60/101,718 filed on Sep. 24, 1998; and U.S. Provisional Application No. 60/107,751 filed on Nov. 10, 1998. This application also claims the benefit of U.S. Provisional Application No. 60/122,949 filed on Mar. 5, 1999. The teachings of each of these referenced applications are incorporated herein by reference in their entirety.

BACKGROUND OF THE INVENTION

A number of different high and low copy number vector systems using a diversity of regulable promoter systems have been successfully developed to manipulate gene expression in Gram negative organisms such as *Escherichia coli*. As a result, *E. coli* can be genetically manipulated in a number of ways that have lead to a thorough understanding of the molecular basis for gene expression and to the elucidation of the function of many important proteins. As a further result, *E. coli* has been used as a production organism for the high level expression of a number of protein products, some of which are toxic. The majority of these vector systems developed in *E. coli*, however, do not function properly in Gram-positive microorganisms, likely due to physiological differences between Gram-positive and Gram-negative species (de Vos, W. M., et al., *Curr. Opin. Biotechnol.* 8:547–553, 1997; de Vos, W. M., and G. F. M. Simons, "Gene cloning and expression systems in lactococci," pp. 52–105. In M. J. Gasson and W. M. de Vos (ed.) *Genetics and Biotechnology of Lactic Acid Bacteria*. Routledge, Chapman and Hall Inc., New York, N.Y., 1994). The lack of vectors providing for the efficiently regulated expression of genes in Gram-positive bacteria has been responsible, in part, for the lack of suitable Gram-positive systems for production of valuable gene products on an industrial scale.

The characterization of the biology of Gram-positive bacteria has been hampered by the lack of cloning and expression vector systems that are stably maintained, tightly regulated and inducible, analogous to those developed in *E. coli*. As a result, the study of important Gram-positive pathogens, that can cause a variety of different illnesses including life threatening ones, has been severely limited, impeding the discovery of novel, life saving therapies to treat infectious diseases.

In the last decade, the rapid rise in severe and fatal infections caused by drug resistant microbial pathogens has presented a significant threat to public health worldwide. One of the pathogens of immediate concern is the Gram-positive organism *Staphylococcus aureus*. There are over nine million cases of *S. aureus* infections a year. *S. aureus* infections are one of the most prevalent types of hospital acquired infections requiring treatment. Methicillin resistant *S. aureus* now represents a significant proportion of all *Staphylococcus aureus* infections in hospitals. Although these infections can be treated with the antibiotic vancomycin, it has been documented that *S. aureus* strains can become resistant to this last line antibiotic. There is genuine concern in the medical community that new antibiotics to treat *S. aureus* infections must be discovered in order to prevent a return to the preantibiotic era where death by bacterial infection was common.

A necessary first step towards the identification of novel therapeutics to treat *Staphylococcus aureus* and other Gram-positive bacterial infections is an ability to clone and regulate the expression of genes in the organism in order to understand its biology. To do this, replicons—replicating units of DNA or RNA, such as plasmids—should be constructed to carry the genes and ensure the desired level of gene expression when the replicons are in the bacterial cells. A system using specially constructed bacterial strains is needed to control and evaluate expression in vitro as well as in vivo during a bacterial infection in an animal model system so that the biology of the infectious disease process can be investigated.

To provide broad practical applications of a Gram-positive inducible gene expression system, it is desirable for the system to have the following features: (1) The system is under tight expression control that avoids or minimizes leaky expression of a cloned gene. Leaky expression can often result in cell toxicity and so must be avoided. (2) The system responds with high levels of expression upon induction. (3) The inducibility of the system is independent of growth media so that a variety of environmental conditions can be evaluated. (4) Administering inducer to the gene expression system, by itself (that is, without production in the cells of the regulated gene product) does not cause significant change in the phenotype of the bacteria (e.g., inhibit the growth of the bacteria). (5) The system functions with features (1), (2), (3) and (4) not only when the bacteria are grown in culture, but also in an animal infection model. To date, there has been no acceptable inducible expression system that covers the above listed criteria. In addition, if improved cloning and expression systems were available a wealth of opportunities could be realized for the efficient and economic utilization of microorganisms for the industrial production of macromolecules.

SUMMARY OF THE INVENTION

The invention encompasses a replicon which can be used for the high-level, inducible production of a gene product in Gram-positive bacteria, including, but not limited to staphylococci (for instance, *S. aureus* and *S. carnosus*), and Gram-positive bacilli (for instance, *Bacillus subtilis*). The invention encompasses a replicon comprising a promoter/operator region that causes gene expression under its control to be tightly repressed in the absence of tetracycline or an analog of tetracycline. However, in the presence of tetracycline or an analog thereof, the promoter/operator region causes a high level of gene expression of a gene situated downstream of the promoter. That is, the promoter/operator can produce a high level of transcription, but is tightly regulated (non-leaky).

Built into the replicon is a linker site downstream of the promoter/operator region so that insertion of a segment of nucleic acid encoding a gene product (wherein the segment comprises an open reading frame) at the linker site can put the transcription of such an open reading frame under the control of the promoter/operator region. Optionally, a linker site can be within or adjacent to a segment of nucleic acid encoding a carrier polypeptide, such that insertion, in frame, of a nucleic acid segment encoding a second polypeptide (which can be as short as a few amino acid residues, and usually termed a "peptide," but here, included in the term "polypeptide") results in a derivative replicon, which when introduced into an appropriate host species of bacteria, can inducibly produce a fusion polypeptide (also, "fusion protein") of the carrier and second polypeptides.

A particular promoter/operator region, called $P_{JT}$/TetO herein, and which has been described herein as a part of $pC^3875$, has been found to be particularly well suited to the tightly controlled tetracycline-regulated expression of genes inserted downstream from the promoter/operator. (Herein, "tetracycline-inducible" or "tetracycline-regulated" describes genetic elements responsive to tetracycline as well as to analogs thereof that act similarly to tetracycline.)

Also an aspect of the invention is a strain of Gram-positive bacteria comprising one or more genes encoding tetracycline resistance [tet(M), tet (0), etc.] and tetR (tet repressor) genes. Construction of such a strain of *S. aureus* is described herein.

A further aspect of the invention is a system for inducible expression of a gene, comprising Gram-positive bacteria bearing a replicon, wherein the replicon comprises a tetracycline-inducible promoter/operator region for the tightly regulated control of gene expression, for example, the promoter/operator $P_{JT}$/TetO (for tet operator, originally described in transposon Tn10, see Wissmann, A. et al., *J. Mol. Biol.* 101:397–406, 1988; also Geissendorfer, M. and W. Hillen, *Appl. Microbiol. Biotechnol.* 33:657–663, 1990), and further comprising an open reading frame downstream of said promoter/operator region, wherein the open reading frame can be a coding sequence for a polypeptide, which can be a fusion polypeptide, for example. The Gram-positive bacteria can be *S. aureus*, for instance.

The replicon of the gene expression system can be constructed to have, instead of an open reading frame immediately downstream of the promoter/operator region, a linker site for the insertion of a segment of nucleic acid comprising a coding region for a gene of interest. The replicon of the gene expression system can also be constructed to have a linker site downstream of the promoter/operator region, wherein the linker is within or adjacent to a coding region for a carrier polypeptide, so that insertion of a second coding sequence results in tetracycline-inducible production of a "carrier-second" fusion polypeptide in cells bearing the replicon.

The system of gene expression described herein is especially well suited to the production of and/or analysis of the effects of gene products that may be toxic to the host cells. The system has further advantages in being suitable for use in an animal testing method. In this method, animals are infected with a strain of engineered bacteria, such as *S. aureus* (herein, the strain of engineered bacteria is an "inducible system for expression of a gene") where the inducible gene encodes a "carrier-peptide" fusion protein. The peptide portion of the fusion protein encoded by the bacterial replicon is a candidate for causing a phenotypic effect on the host bacterial cells, typically, by enhancement or inhibition of the function of a host cell component, such as the activity of a host bacterial cell enzyme, resulting in a slowing or cessation of growth of the host bacterial cells. Tetracycline or inducing derivatives or analogs thereof can be safely given to the infected animals, to induce the controlled production of the "carrier-peptide" fusion protein. If the tetracycline induction of gene expression of the "carrier-peptide" fusion protein produces a slowing or cessation of growth of bacterial cells infecting the test animals (resulting in animal survival), then the peptide portion of the fusion protein is proven effective as having antibiotic action. It can be concluded then, also, that the peptide portion is affecting a target cell component that is essential to growth of the bacterial cells. Further measures can be taken to find more physiologically stable structural analogs of the peptide or to otherwise develop antibiotics modeled on the structure of the peptide.

DETAILED DESCRIPTION OF THE INVENTION

Figure 1A:
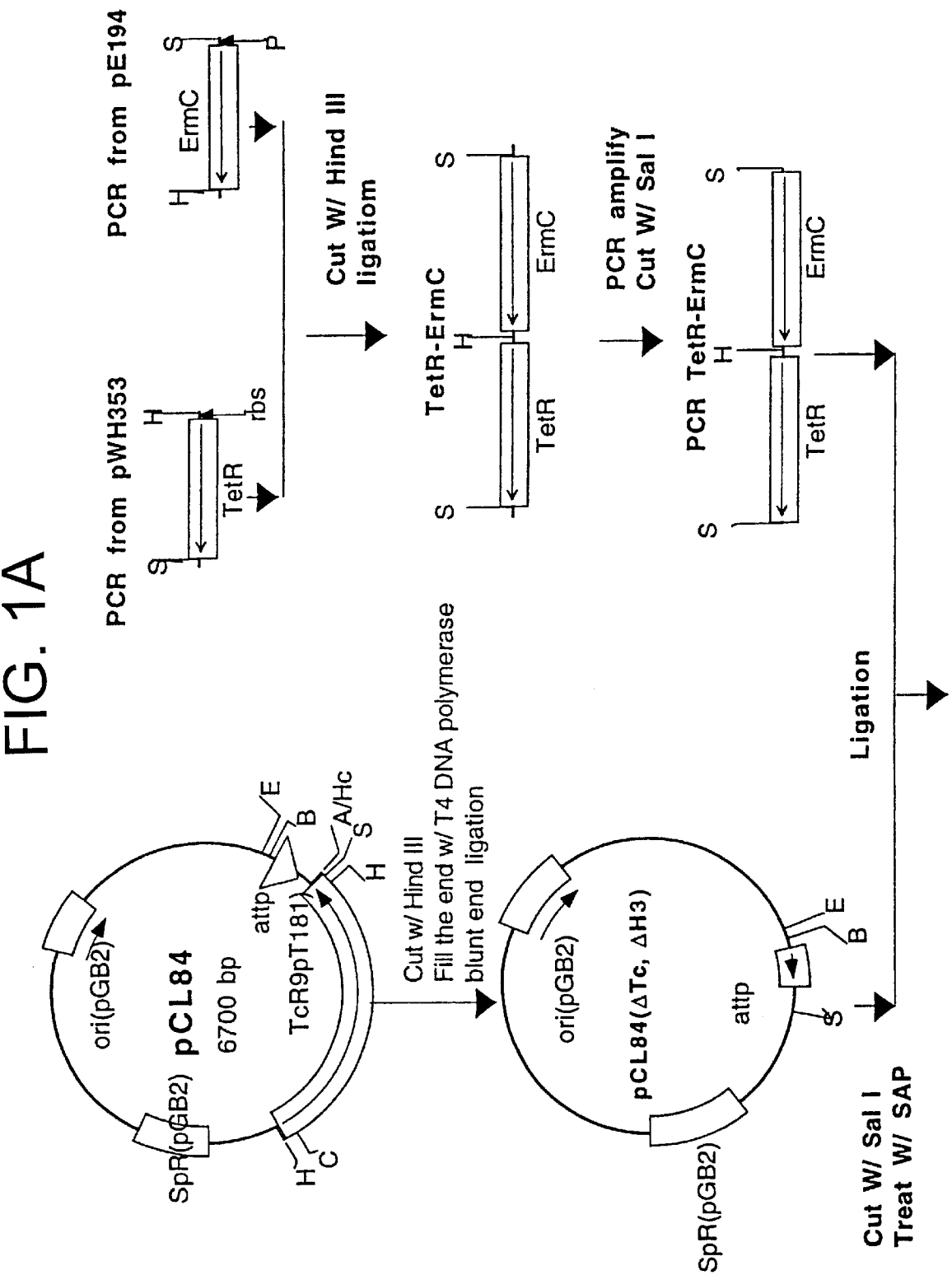
FIGS. 1A–1B is a diagram of the steps taken to construct plasmid pCL84tt, which was then used in the construction of *S. aureus* strain CYL316. Pestricrion sites on the plasmids are indicated as follows: E=FcoRI; H=HindIII; S=SalI. P indicates promoter.

The invention includes replicons suited to use for the expression of a desired gene and the production of one or more gene products, wherein the gene product can be mRNA, tRNA, rRNA, but is preferably a polypeptide (e.g., a peptide or a protein, such as an enzyme) including a fusion polypeptide, in bacteria. Replicons can include, for example, plasmids, phagemids, cosmids, genetically engineered bacteriophages or viruses of appropriate host range. A replicon can be single-stranded or double-stranded DNA or RNA or modified variants thereof, which can, for some purposes, include modified or synthesized bases, and bases not found in nucleic acids isolated from sources found in nature. A replicon can be a discrete unit of nucleic acid that replicates independently of the chromosome of its host bacterial cell, ("replicon" herein excludes the chromosome of the bacterial cell) and can be present as a single copy or as multiple copies. In each case, the elements necessary for replication of the replicon nucleic acid are found in the nucleic acid of the replicon or can be found in the host bacterial cells containing the replicon, so that the replicon ("replicon" encompassing the plural, as a great number are usually present in cultures of cells or as the isolated nucleic acid) can be produced within the bacterial cells from one generation to the next, or can be produced and recovered in a form that can be introduced into bacterial cells of a culture different from that in which they reproduced, to initiate further rounds of replication.

Gram-positive bacteria are those which can be identified by the well-known Gram staining method, and include, for example, *Staphylococcus aureus, Staphylococcus carnosus, Staphylococcus epidermidis, Staphylococcus saprophyticus, Streptococcus pyogenes, Streptococcus agalactiae, Streptococcus pneumoniae, Streptococcus salivarius, Streptococcus mitior, Streptococcus milleri, Streptococcus sanguis, Streptococcus mutans, Corynebacterium diphtheriae, Corynebacterium hemolyticum, Enterococcusfaecalis, Enterococcusfaecium, Enterococcus avium, Enterococcus casseliflavus, Enterococcus durans, Enterococcus gallinarum, Enterococcus molodoratus, Enterococcus affinosus, Enterococcus pseudoavium, Enterococcus solitarius, Enterococcus mundtii, Enterococcus hirae, Listeria monocytogenes, Bacillus anthracis, Clostridium perfringens*, and *Clostridium difficile*.

The replicon of the invention comprises several elements which are encoded in the order of nucleotides of the nucleic acid of the replicon. These elements can be sites necessary for replication of the replicon, such as an origin of replication, having one or more sites for recognition by a DNA polymerase. Other sites can include a promoter/operator region, which can have one or more sites to which a repressor can bind (operator) to regulate transcription initiating at the promoter, and one or more sites for recognition of RNA polymerase (promoter). Downstream from the promoter (that is, in the direction of travel of RNA polymerase from the promoter during transcription-5' to 3' with respect to the sense strand) can lie a linker site, which can be one or more restriction sites (cleavable by use of one or more restriction enzymes under conditions appropriate for restriction enzyme activity). A linker site can be positioned such that it lies outside of any desired coding sequence, in which case it can be used for the insertion of a segment of nucleic acid having a sequence encoding a gene product. In an alternative arrangement, for producing a fusion polypeptide, a linker site can be positioned such that it lies within or adjacent to a first sequence encoding a first polypeptide (which is sometimes called a "carrier" protein or polypeptide), such that insertion into the linker site of a segment of nucleic acid having a second sequence encoding a second polypeptide results in a gene which encodes, under the regulation of the promoter/operator region, a fusion polypeptide having an amino acid sequence encoded, in part, by the first nucleic acid sequence, and in part, by the second nucleic acid sequence.

Some embodiments of the replicon are nucleic acid replicons that replicate in host cells of one or more species of Gram-positive bacteria, each replicon comprising an inducible gene which does not encode chloramphenicol acetyltransferase or tet repressor, wherein expression of said gene is non-leaky, and wherein expression of said gene is high level in the host cells under inducing conditions.

A further embodiment is a nucleic acid replicon that replicates in one or more species of bacteria, said replicon comprising a tetracycline-inducible promoter/operator region, wherein the promoter of said promoter/operator region does not control production of tet repressor or chloramphenicol acetyltransferase, and further comprising a linker site downstream of the promoter/operator region such that insertion, in frame, of a nucleic acid segment encoding a gene product results in a derivative replicon in which production of the gene product in the bacteria is under tetracycline-inducible control by the tetracycline-inducible promoter/operator region in said replicon.

The term "polypeptide" is not intended to be limiting as to the number of amino acid residues. Peptides as short as three amino acid residues are included within the term "polypeptide" as used herein. Polypeptides can have amino acid sequences that are the same as, or similar to, those of proteins and polypeptides found in natural sources, or they can have amino acid sequences that are the product of the invention of humans. Polypeptides produced in cells can also have post-translational modifications such as phosphorylation or removal of a portion by enzymatic cleavage.

It is known that many antibiotics exert their physiological effect by binding to, and inhibiting the function of, a component of a cell which is the target of treatment. For example, the target cell component can be an enzyme, and the inhibitor can bind to the active site, or near to, the active site so as to inhibit the activity of the enzyme. The inhibitor can also, for example, bind to a site on a protein necessary for interaction with another protein or a cofactor which is necessary for normal function of the protein. The result of binding of an inhibitor to its target site is a phenotypic effect on the cell ("cell" includes cells of a cell culture or cell strain), which as desirable for an antibiotic, can be slowing or cessation of cell growth. In the case of an inhibitor which binds to and inhibits the function of a target cell component of a species of pathogenic bacteria, without or only minimally binding to and inhibiting the function of a cell component of a mammal which can be infected by the pathogenic bacteria, the inhibitor is displaying a function as an antibiotic, and can be the basis for further study (e.g., rational drug design based on the structure of the inhibitor, or screening of libraries of compounds to discover those that may have similar binding to the target site of the inhibitor).

A polypeptide to be encoded under the (transcriptional) control of the promoter/operator region of the replicon, whether the polypeptide is a fusion polypeptide or is a nonfusion polypeptide, can be, for example, a candidate molecule to be tested for inhibition of enzyme activity of a host bacterial enzyme, upon induction of gene expression and production of the polypeptide. The inducible expression controlled by the regulated promoter/operator region makes a replicon that is suitable for the expression of polypeptides that are toxic to the host cells when made in sufficiently large quantities. Therefore, the replicon of the invention is well suited to a test, in bacteria, of polypeptides that, as explained above, are candidates for having antibiotic activity.

The first polypeptide of a fusion polypeptide can be, for example, glutathione S-transferase (GST) of *Schistosoma japonicum*. GST coding sequences have been described and are available as part of gene fusion vectors available from Pharmacia (Uppsala, Sweden). The first polypeptide of a fusion polypeptide can be, for example, green fluorescence protein (GFP), maltose binding protein (MBP), protein A, or β-galactosidase, cellulose binding domain (Novagen), chitin binding domain (New England Biolabs), a polypeptide including a His-Tag affinity ligand (pET series plasmids, Novagen), Flag-Tag, or a sufficiently long portion of a polypeptide such that affinity binding characteristics of the carrier portion can be used to advantage in the purification of a fusion protein comprising such portion of a carrier polypeptide.

The replicon can further comprise other components within its nucleic acid, including, for example, a selectable marker gene. For example, a gene encoding a protein that confers upon the host bacterial cells resistance to an antibiotic, can be used as a device to ensure maintenance of the replicon in the host cells over many generations of growth of the host bacterial cells.

Also an embodiment of the invention is a system for the expression of a gene, resulting in the production of a gene product, comprising host bacterial cells which comprise a replicon as described above. The system can carry, in addition to those genetic components incorporated into the replicon, genetic components, present in one or more copies, incorporated into the chromosome of the host bacterial cells or carried on another replicon. The location of the genetic components is not critical, except that the placement of the tetracycline promoter/operator region and the coding region to be under its control be such that production of the gene product is controlled by tetracycline induction of the default repressed condition. The distance between the promoter/operator region and the coding region or open reading frame can vary among effectively controlled systems, and can be determined by one of ordinary skill in the art. In the case of a system carrying on the replicon a promoter/operator region controlling transcription by induction with tetracycline or a suitable analog of tetracycline, such as anhydrotetracycline, the system can have incorporated into it a gene encoding a product which confers a tetracycline resistant phenotype on the host bacterial cells, such as the tet(M) tetracycline resistance gene (Burdett, V., *J. Biol. Chem.* 266:2872–2877, 1991), or the tet(O) tetracycline resistance gene (Manavathu, E. K. et al., Gene (Amst.) 62:17– 6, 1988). Such a gene can be carried on the replicon, on the bacterial chromosome, or on some other extrachromosomal element.

The tet(M) tetracycline resistance gene was initially identified in streptococci Burdett, V. et al., *Microbiology* 1982 (Schlessinger, D., ed.) pp. 155–158, American Society for Microbiology, Washington, D.C.), but has also been identified in staphylococci (Bismuth, R. et al., *Antimicrob. Agents Chemother.* 34:1611–1614, 1990), *Clostridia difficile* (Hachler, H. et al, *Antimicrob. Agents Chemother.* 31:1033–1038, 1987), *Neisseria gonorrhoeae* (Morse, S. A. et al, *Antimicrob. Agents Chemother.* 30:664–670, 1986), and mycoplasmas (Roberts, M. C. et al, *Antimicrob. Agents Chemother.* 28:141–143, 1985); it has been cloned and expressed in *Bacillus subtilis* (Clewell, D. G. and Gawron-Burke, C., *Annu. Rev. Microbiol* 40:635–659, 1986; Courvalin, P. and Carlier, C., *Mol. Gen. Genet.* 205:291–297, 1987) and *Escherichia coli* (Burdett, V. et al., *J. Bacteriol.* 149:995–1004, 1982). Other genes are known to produce a tetracycline resistant phenotype and can be used in the gene expression system of the invention; a tet(O) gene has been characterized, in addition to tet(M), in *Streptococcus faecalis* (Burdett, V., *J. Bacteriol.* 165:564–569, 1986).

In addition to a gene conferring tetracycline resistance on the host bacterial cells of the gene expression system, the system can also carry one or more genes which encode a repressor of the tetracycline-inducible promoter/operator ("tet repressor" or "tetracycline repressor"). Such repressor genes can be inducibly expressed (for example, by a tet promoter/operator), but are preferably constitutively expressed.

The invention also provides a system for the production of a gene product that is tightly regulated or tightly controlled—that is, the system does not suffer from "leaky" gene expression. In this way, a gene product that causes some degree of toxicity to the cells, can be produced in the cells of the system only when it is desired, and the genetic content of the cells can be stably maintained from one generation to the next without the danger of selection against those cells expressing a product which can inhibit growth and replication of the cells.

Preferably, the system responds to the induced condition with a high level of production of the gene product, relative to the uninduced condition. The level of production of the gene product can be assayed by, for example, assays of enzymatic activity (e.g., aminoacylation activity by an aminoacyl-tRNA synthetase), by quantitation of purified gene product (for instance, by determinations of protein concentration, quantitation of protein labeled with a radioactive isotope or a fluorescent tag). In a preferred embodiment, the system responds to induction of gene expression with a high level of gene expression, by producing a high level of gene product (e.g., per unit of cells or cell lysate, total cell protein, or total cell RNA, etc., as appropriate) which is at least about 10 times the uninduced level; in a more preferred embodiment, at least about 100 times the uninduced level; in a still more preferred embodiment, at least about 1,000 times the uninduced level; and most preferably, at least about 10,000 times the uninduced level.

The invention also provides a system which can accommodate the production of a wide variety of gene products in Gram-positive bacteria, which has not been demonstrated, for example, with a system employing the plasmids of Hillen et al. (DE 3934454 A1; Geissendorfer, M. and W. Hillen, *Appl. Microbiol. Biotechnol.* 33:657–663, 1990). A desirable property of the system of the invention is that administering inducer to the gene expression system (even before, or in the absence of the biosynthesis of the controlled gene product), does not cause a significant change in the phenotype of the cells—that is, a change that is an effect detrimental to growth or some effect that can mask the effect on the phenotype of the induced gene product.

The invention further provides a system in which expression of a gene of interest can be efficiently induced in rich, complete media [for example, Luria-Bertani broth (LB), NZ-amine, Voges-Proskauer broth, nutrient broth, trypticase soy broth, Robertson's cooked meat medium; see, for instance, *Bergey's Manual of Systematic Bacteriology*, (P. H. A. Sneath et al., eds.), Williams and Wilkins, Baltimore, Md., 1986], as well as in minimal media (essential salts, including a nitrogen source, and a sugar to supply a carbon source). Other systems for the regulated expression of a gene and production of a polypeptide have been described in Gram-positive bacteria. For example, a pBla/BlaR system in *S. aureus* has been described, although this system has suffered from instability of plasmids. A system in *B. subtilis* has been described which employs the *E. coli* lac operon (Yansura, D. G., and D. J. Henner, *Proc. Natl. Acad. Sci. USA* 81:439–443, 1984). A system for regulated gene expression which employs an inducible xyl operon has been tried in staphylococci (Sizemore, C. et al., *FEMS Microbiology Letters* 107:303–306, 1993). A system for the nisin-inducible expression of a gene regulated by the lactococcal nisA promoter has been described for *Streptococcus pyogenes* and for *Bacillus subtilis* (Eichenbaum, Z. et al., *Applied and Environmental Microbiology* 64:2763–2769, 1998).

The invention also provides a gene expression system which can be used for the testing of the phenotypic effect of a gene product upon the host bacterial cells in which its biosynthesis occurs, upon regulated production of the gene product. The phenotypic effect of the gene product may be, for example, the enhancement or inhibition of activity of an enzyme, which, in some cases, can cause an inhibition of growth of the host bacterial cells.

Figure 4:
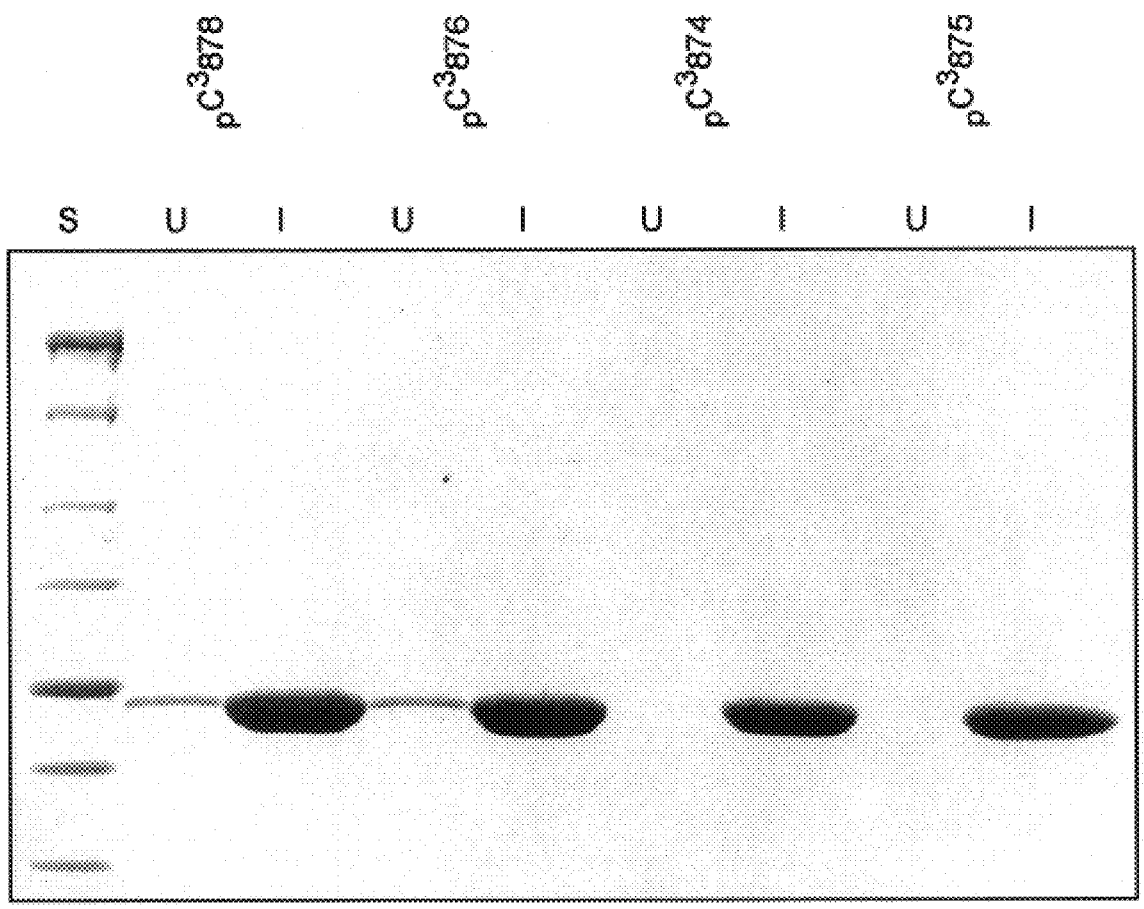
FIG. 4 is a scan of an SDS-polyacrylamide gel, stained with Coomassie blue, which was loaded with the glutathione-Sepharose-purified proteins produced under induction conditions ("I" lanes) or uninduced conditions ("U" lanes) in CYL316t/$pC^3878$, CYL316t/$pC^3876$, CYL316t/$pC^3874$ and CYL3 16t/$pC^3875$. Glutathione S-transferase is the prominent band.

The testing of phenotypic effect can be done in culture, using inducer to turn on gene expression and thereby, production of the gene product. The phenotypic effect can be observed by various assays (e.g., monitoring an enzymatic activity, growth rate, level of a metabolite or intermediate in a biosynthetic pathway) on the induced culture of bacterial cells, comparing the results with those of an uninduced culture. For an optimal test of phenotypic effect, the basal (uninduced, or repressed) level of gene expression should be minimal, so that gene expression is not "leaky." That is, the basal level of the gene product of the regulated gene of a non-leaky system is such that the phenotypic effect expected in the induced cells is not observed, or not observed to a significant extent (e.g., a statistically significant extent) over cells not containing the gene. It is preferable that the basal level of the gene product of the regulated gene of the system is undetectable as a band on an SDS-polyacrylamide gel stained with Coomassie blue, as it was for an expression system containing pC$^3$875 (see Example 3 and FIG. 4). In one embodiment, the basal level of the encoded gene product of the gene expression system is less than about 100 $\mu$g/ml of initial wet cell weight; in preferred embodiment, less than about 10 $\mu$g/ml; in a more preferred embodiment, less than about 100 ng/ml, and in an even more preferred embodiment, less than about 10 ng/ml.

The testing of phenotypic effect can be done in an animal model, as well as in Gram-positive bacterial cells grown in culture. See U.S. patent application Ser. No. 09/227,687, the teachings of which are incorporated by reference herein. For an engineered strain of Gram-positive bacterial cells to be used in the gene expression system of the invention, an object of the test can be to see whether production of the gene product in the engineered strain inhibits growth of these cells after the introduction of the cells into one or more animals. Suitable animals for such an experiment are, for example, mammals such as mice, rats, rabbits, guinea pigs, dogs, pigs, and the like. Small mammals are preferred for reasons of convenience. The engineered Gram-positive bacterial cells of the inducible gene expression system are introduced into one or more animals ("test" animals) and into one or more animals in a separate group ("control" animals) by a route appropriate to cause symptoms of systemic or local growth of the engineered cells (infection). The route of introduction may be, for example, by oral feeding, by inhalation, by subcutaneous, intramuscular, intravenous, or intraperitoneal injection as appropriate to the desired result (e.g., location and severity of infection).

After the Gram-positive bacterial cells of the inducible gene expression system of the invention have been introduced into the test and control animals, expression of the gene encoding the gene product of interest is regulated to allow production of the gene product in the engineered pathogen cells. This can be achieved, for instance, by administering to the test animals a treatment appropriate to the regulation system built into the cells, (e.g., administering tetracycline or an appropriate analog such as anhydrotetracycline) to cause the gene encoding the gene product of interest to be expressed. The same treatment is not administered to the infected control animals, but the conditions under which they are maintained are otherwise identical to those of the test animals.

After such treatment, the test and control animals can be monitored for a phenotypic effect in the introduced cells. The animals can be monitored for signs of infection with the engineered Gram-positive bacterial cells of the tetracycline-inducible gene expression system of the invention (as the simplest endpoint, death of the animal, but also e.g., lethargy, lack of grooming behavior, hunched posture, not eating, diarrhea or other discharges; bacterial titer in samples of blood or other cultured fluids or tissues). If the test animals are observed to exhibit less growth of the introduced cells than the control animals, then it can be concluded that the expression in vivo of the gene product of the regulated gene is the cause of the relative reduction in growth of the introduced cells in the test animals, and that the gene product is interfering with a target cell component whose function is necessary to the normal growth of the introduced cells.

"In culture" and "in animal" tests for the effect of a gene product expressed upon induction of the gene expression system as described above can be done in succession, or concurrently. Following an animal test as described above, further steps can be taken involving in vitro assays to identify one or more compounds that have binding and activating or inhibitory properties that are similar to those of the gene product which has been found to have a phenotypic effect when produced intracellularly, such as inhibition of growth. That is, compounds that compete for binding to a target cell component with the gene product tested would then be structural analogs of that gene product and could be, for example, candidates for antibiotic activity. Assays to identify such compounds can take advantage of known methods to identify competing molecules in a binding assay.

Thus, the test in an animal model as described above is a method that can be used to confirm that a gene product, inducibly produced in the Gram-positive bacteria, can function as an antibiotic under conditions of an infection. The system of inducible gene expression described herein (that is, the Gram-positive bacteria bearing replicons as described herein) is especially well-suited to use in the test of the effect of the inducible gene product, in an "in animal" test (infection) as well as in an "in culture" test. The system has the following advantages for an "in animal" test.

(1) The inducible gene expression system does not require specially-formulated media (for instance, a minimal salts medium or a special change of carbon source for induction). The inducible system works well in the rich medium supplied by animal biological fluids, as well as in defined medium.

(2) The induction method alone has no measurable effect on mice. Nor does adding inducer (or an analog thereof that has the same effect as the inducer) to the bacteria of the gene expression system, alone—that is, in the absence of production of the induced gene product—cause any measurable phenotypic change in the bacteria.

(3) The inducible gene expression system as described herein is a) tightly controlled, and b) inducible to a high level of intracellular gene product, making the results of an "in animal" test clearly interpretable. Complete inhibition of the Gram-positive bacterial cell target is possible for an effective inhibitor of an essential target cell component. This can result in sparing of the infected test animals in which gene expression of the regulated gene is induced, compared to no effect in the control animals (course of infection is not altered, resulting in death).

One of ordinary skill in the art can adapt the replicon described herein to make use of the promoter/operator region (for instance, the promoter/operator region of pC$^3$875, designated P$_{JT}$/TetO) and optionally, a coding region for a fusion polypeptide, by inserting it into replicons having different origins of replication, and therefore, different host ranges. The P$_{JT}$/TetO-GST region of pC$^3$875 can be excised from pC$^3$875 using EcoRI digestion or digestion with BstEII and SpeI, for insertion into sites of different replicons. See map of pC$^3$875 in FIG. 2.

A large number of plasmids capable of replicating in *S. aureus* have been identified, such as pC194, pT181, pSN2, and pE194 (Novick, R. P., *Methods in Enzymology* 204:587–637, 1991). Many of these plasmids are also capable of replicating in other Gram-positive species (e.g., *Staphylococcus carnosus, Bacillus subtilis*, and subspecies of Lactococcus). Additional examples of plasmids to be modified by insertion of P$_{JT}$/TetO or P$_{JT}$/TetO together with an open reading frame of interest, include pAM401 (ATCC No. 37429; an *E. faecalis/E. coli* shuttle vector), and *Streptococcus pneumoniae* plasmids pLSE4 (ATCC No.37819), pLS21 (ATCC No. 67492), and pLS101 (ATCC No. 39938).

One of ordinary skill in the art recognizes that certain functional regions and nucleotide sequence features are common to promoters and operator regions of bacteria and that some of these nucleotide sequence features are more particular to one species or group of species. See, for example, Lewin, pages 302-305 In *Genes*, Oxford University Press, 1997. Thus, it is possible to produce variants of P$_{JT}$/TetO, which differ from in nucleotide sequence from that of P$_{JT}$/TetO, but which retain the functional characteristics of as a control region. Variants include those promoter/operator regions that differ from P$_{JT}$/TetO by the substitution, deletion, or insertion of one or more nucleotides, especially within non-consensus sequences. Such variants of P$_{JT}$/TetO are also included in the invention.

EXAMPLES

Example 1

Figure 1B:
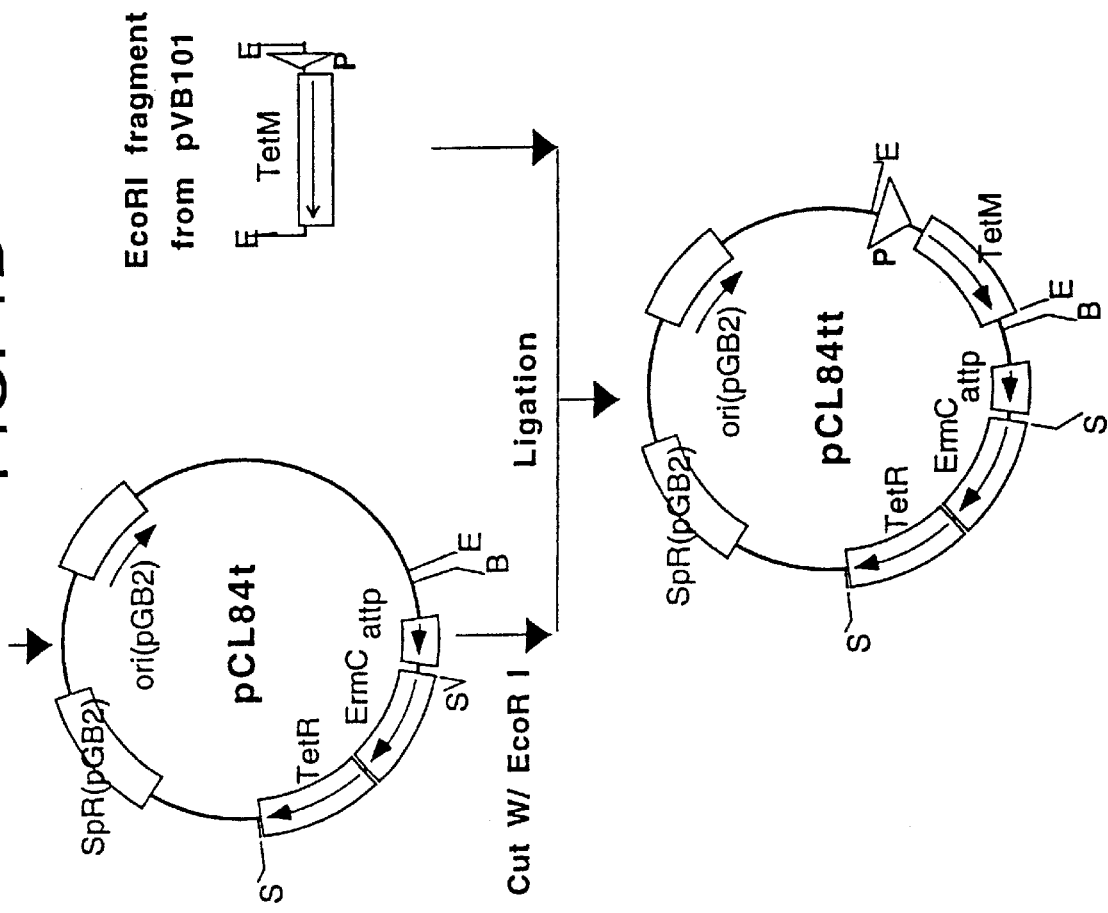

Construction of *Staphylococcus aureus* Strains That Constitutively Express the Tet Repressor, TetR Construction of pCL84(ΔTc, ΔH3)

pCL84 is a *S. aureus* chromosome integration plasmid (Lee, C. Y. et al., *Gene* 103:101–105, 1991) and was used for integration of the tet repressor gene into the *S. aureus* chromosome. pCL84 carries a tetracycline resistance gene (ret(K)) that is derived from plasmid pT181 (Guay, G. G. et al., *Plasmid* 30:163–166, 1993). Since this tetracycline resistance gene encodes a protein that acts as a tetracycline efflux pump, which is not desirable for a tetracycline inducible expression system, the following steps were taken to eliminate this gene from pCL84. Plasmid construction steps are diagramed in FIGS. 1A–1B. pCL84 was digested with restriction endonuclease HindIII, and the resulting HindIII overhangs were blunted using T4 DNA polymerase. The DNA sample was then subjected to agarose gel electophoresis to separate the fragments. The "vector" portion (carrying the origin of replication, the gene encoding spectinomycin resistance, and attP) was purified using GeneClean (Bio 101), ligated using T4 DNA ligase, and transformed into *E. coli* NovaBlue cells (Novagen). Plasmids isolated from three of the resulting transformants were tested by restriction endonuclease HindIII or SalI digestion, and all three were confirmed to be pCL84 devoid of the Tc$^R$ gene. One of these three plasmids was named pCL84(ΔTc, ΔH3) and was used in further procedures described below.

Construction of an ermC and tetR Transcription Fusion Gene in pCL84(ΔTc,ΔH3)

The ermC gene, including its promoter, was amplified from plasmid pE194 (ATCC No. 68359) using Taq DNA polymerase with oligonucleotide primers ermC-5' (5'acgggtcgactcatatctttattcaataatcg; SEQ ID NO:1) and ermC-3' (5'ccggaaagcttacttattaaataatttatagc; SEQ ID NO: 2). The tetR gene was amplified from plasmid pWH354 (DE 3934454 A1; Geissendörfer, M. and W. Hillen, *Appl. Microbiol. Biotechnol.* 33:657–663, 1990) using Taq DNA polymerase with primers tetR-5' (5'taagtaagcttaaggaggaattaatgatgtctag; SEQ ID NO:3) and tetR-3' (5'acgggtcgacttaagacccactttcacatttaag; SEQ ID NO:4). The amplified tetR gene carried a synthetic ribosomal binding site. These two PCR products were purified with the Wizard PCR Preparation Purification Kit (Promega), digested with HindIII restriction endonuclease, and ligated together with T4 DNA ligase. The resulting ligated DNA was then used as the template for PCR amplification using Taq DNA polymerase with primers ermC-5' and TetR-3'. The PCR product was purified with the Wizard PCR Preparation Purification Kit (Promega), digested with SalI restriction endonuclease to make SalI ends, and then further purified with Wizard PCR Preparation Purification Kit (Promega). The purified ermC-tetR fusion gene was then ligated to SalI-digested, shrimp alkaline phosphatase (SAP) treated, and gel purified pCL84(ΔTc,ΔH3). The ligated DNA was transformed into *E. coli* NovaBlue cells (Novagen). Fifty-five transformants were subjected to colony PCR screening using primers ermC-5' and tetR-3'. Two clones, pCL84t #16, and #19, were identified as containing the ermC-tetR fusion gene. Plasmid DNA was purified from these two clones and the tetR gene sequence in clone #16 was confirmed by DNA sequencing. The ErmC gene provides not only a selectable phenotypic marker (erythromycin resistance), but also a constitutive promoter for the TetR gene.

Integration of ermC-tetR Fusion Gene Into the *S. aureus* Chromosome

Plasmid DNA isolated from clone #16 was transformed into *S. aureus* CYL316 cells by electroporation (Schenk, S. and R. A. Laddaga, *FEMS Microbiology Letters* 94:133–138, 1992). The transformation was spread on LB plates containing 10 μg/ml of erythromycin. Six transformants were isolated and it was confirmed by a lipase assay (Lee, C. Y. et al., Gene 103:101–105, 1991) that ermC-tetR was integrated into the phage L54a integration site on the chromosome in all six. The resulting clones were designated strain CYL316t. The expected structure was confirmed by PCR experiments.

Confirmation of tetR expression in the CYL316t *S. aureus* strain

Overnight cultures of *E. coli* DH5αPRO, and cultures of *S. aureus* RN4220 (Novick, R. P. et al., *Methods in Enzy-*

*mology* 204:587–637, 1991) carrying pWH354, *S. aureus* strain CYL316t, or CYL316:pCL84 were diluted 60-fold in 2 tubes of fresh LB containing 50 μg/ml spectinomycin (for DH5αPRO), 25 μg/ml kanamycin (for RN4220/pWH354), 10 μ/ml erythromycin (for CYL316t), or 3 μg/ml tetracycline (for CYL316:pCL84) and grown at 37° C. At 2.5 hours, anhydrotetracycline was added to one set of cultures to 200 ng/ml. The cells were grown for an additional 3 hours. The cells were pelleted from 3 ml of culture and resuspended in 200 μL of 1×PBS containing 50 μg/ml lysostaphin. After incubating at 4° C. for 30 minutes, the cell suspensions were subjected to three freeze-thaw cycles between a dry-ice/ethanol bath and a 37° C. water bath, followed by a 15-second sonication with a microtip. The cell lysates were then boiled in SDS-PAGE sample buffer and subjected to electrophoresis on a 12.5% SDS-polyacrylamide gel. The separated proteins were then blotted to a nitrocellulose membrane and analyzed by Western blot using an anti-Tet repressor protein antibody (kindly provided by Prof. Wolfgang Hillen). The results confirmed that tetR is constitutively expressed in *S. aureus* strain CYL316t.

Construction of a *Staphylococcus aureus* Strain That Constitutively Expresses tetR as Well as tetM An EcoRI fragment containing the tet(M) gene of Tn916 was isolated from plasmid pVB101, a construct similar to pVB201 (Burdett, V., *J. Bacteriol.* 175:7209–7265, 1993). The tet(M) gene fragment was cloned into the EcoRI site of pCL84t, resulting in plasmid pCL84tt. pCL84tt was integrated into the *S. aureus* chromosome in CYL316, resulting in strain CYL316tt. CYL316tt can grow in LB medium containing 10 μg/ml tetracycline.

Example 2

Construction of Expression Plasmids

Figure 2:
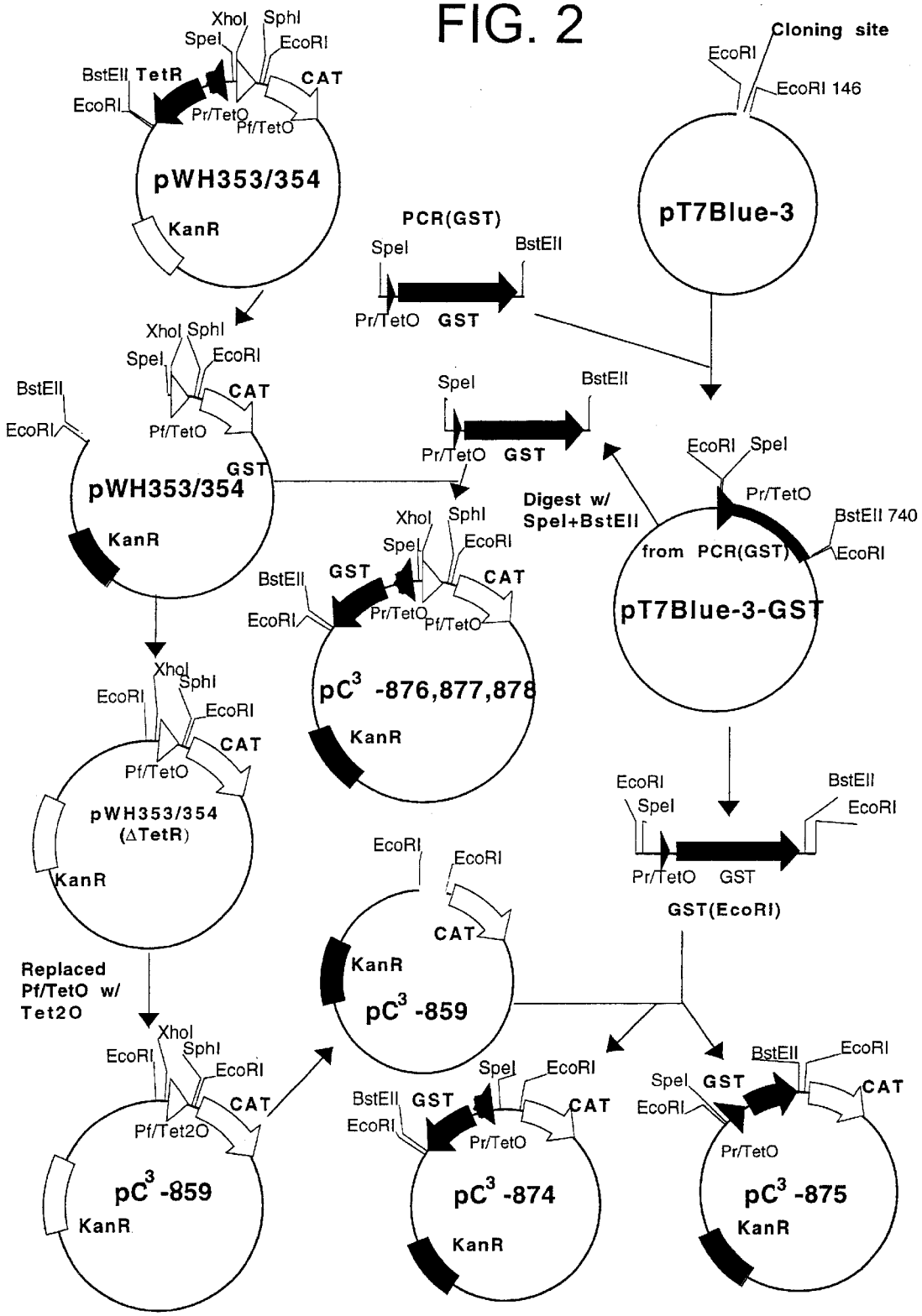
FIG. 2 is a diagram of the steps taken to construct plasmids $pC^3874$ and $pC^3875$.

The steps in plasmid construction are diagramed in FIG. 2.

A. pWH353 and pWH354 Derivatives

*E. coli/Bacillus subtilis* shuttle expression vectors pWH353 and pWH354 were obtained from Professor Wolfgang Hillen (Mikrobielle Genetik, Universität Tübingen, T übingen, Germany; DE 3934454 A1; Geissendörfer, M. and W. Hillen, *Appl. Microbiol Biotechnol.* 33:657–663, 1990). These expression vectors carry a Tn10 tetR gene encoding Tet repressor. They also contain synthetic promoters with one or two Tet repressor binding sites that are optimized for inducible expression in *B. subtilis*. These inducible promoters direct the expression of a chloramphenicol acetyltransferase (CAT) gene in each case.

The CAT gene in pWH353 or pWH354 was replaced with a GST gene. The GST gene was PCR amplified with Taq DNA polymerase using pGEX-4T-2 as the template and the combination of oligonucleotide primers 2a-5'-GST (5' CTC GGT ACC GAG CTA AAA TTC GGA GGC ATA TCA AAT GAG CTC TGG) (SEQ ID NO:5), 2b-5'-GST (5'GGC ATA TCA AAT GAG CTC TGG AGG TGG AGG CAT GTC CCC TAT AC) (SEQ ID NO:6), and 3'-GST-AvrII (5'AGG CCT AGG TTA ATC CGA TTT TGG AGG ATG G) (SEQ ID NO:7) as the primers. The PCR fragment was cloned into pT7Blue(T) vector (Novagen). The GST gene in the resulting pT7Blue(T) vector was then excised by KpnI and StuI double-endonuclease digestion and further cloned into the KpnI/StuI sites of pWH353 and pWH354, resulting in pWH353-2G, and pWH354-2G. A synthetic gene encoding peptide JT101 was obtained by annealling oligonucleotides M1.Sac.a (5' CTG ATC CGA ATA CGT GGC AGT TGC GGT GGC CTA TGC ATA GCT) (SEQ ID NO:8) and M1.Sac.b (5' ATG CAT AGG CCA CCG CAA CTG CCA CGT ATT CGG ATC AGA GCT) (SEQ ID NO:9) and cloned into the SacI site of pWH353-2G and pWH354-2G. Clones pWH353-2G-M1 and pWH354-2G-M1 were identified that contained the M1-GST fusion gene.

B. pWH353(ΔtetR) and pWH354(ΔtetR) and Their derivatives

Plasmids pWH353, pWH354 and pWH354-2G were each digested with restriction endonucleases SpeI and BstEII, which excise a DNA fragment encompassing the tetR gene in these two plasmids. The overhangs of the resulting DNA fragments were blunted using T4 DNA polymerase. The "vector" portion of each of these two digestions (the remainder of the plasmid without tetR) was gel purified, self-ligated using T4 DNA ligase, and was then transformed into *E. coli* NovaBlue cells (Novagen). Clones carrying pWH353 or pWH354 or pWH354-2G deleted for the tetR gene were identified by PCR colony screening, and were designated pWH353(ΔtetR), pWH354(ΔtetR) and pWH354-2G(ΔtetR), respectively.

C. pC$^3$859 and Its Derivatives

The following four oligonucleotides were chemically synthesized: Tet-2OF: 5'tcgagttcatgaaaaac-taaaaaaaatattgacatccctatcagtgat (SEQ ID NO:10) Tet2/3OF: 5'agagataattaaaataatccctatcagtgatagagagcttgcatg (SEQ ID NO:11) Tet2/3OR: 5'caagctctctatcactgatagggattatt (SEQ ID NO: 12) Tet2OR: 5'ttaattatctctatcactgatagggat-gtcaatattttttttagttttttcatgaac (SEQ ID NO:13) Oligonucleotides Tet-2OR and Tet-2/3OF were phosphorylated using T4 polynucleotide kinase. Equal molar amounts of the phosphorylated Tet-2OR, Tet-2/3OF, and unphosphorylated Tet-2OF, Tet-2/3OR were mixed together, heated to 85° C. for 5 minutes and cooled down to room temperature gradually in a 2-hour period. The annealed oligonucleotides, called Tet-2O, comprised a synthetic promoter with two tet2O operator sequences that are derived from Tn10.

pWH354(ΔtetR) was digested with restriction endonucleases XhoI and SphI, which excised the promoter/operator that controlled CAT expression. The digested DNA was separated on a 1% agarose gel. The DNA fragment of the vector portion was purified and ligated with Tet-2O DNA fragment. The ligation was transformed into DH5αPRO (Clontech). A clone of the desired recombination was identified and designated pC$^3$859.

The CAT gene open reading frame in pC$^3$859 was substituted with the GST gene amplified from plasmid pGEX-4T-2 (Pharmacia), green fluorescence protein (GFP) gene amplified from pQBI63 (Quantum Biotechnologies), or maltose binding protein amplified from pMAL-c2 (New England Biolabs), resulting in plasmid pC$^3$859-GST, pC$^3$859-GFP, and pC$^3$859-MBP respectively.

D. pC$^3$876 and pC$^3$878

The GST gene was PCR amplified with Taq DNA polymerase from plasmid pGEX-4T-2 with the following 3 primers:

1-5'-GST(TetR): 5'aataaaaaactagtttgacaaataactc-tatcaatgatagagtgtcacaaaaaggagg (SEQ ID NO:14)
2-5'-GST(TetR): 5'gatagagtgtcaacaaaaaggaggaat-taatgatgtcccctatactaggttattgg (SEQ ID NO:15)
3'-GST(TetR): 5'ggattaaggtaaccttaatccgattttggaggatgg (SEQ ID NO:16)
2-5'-GST(TetR) can anneal to the 5'end of GST and amplify the GST gene along with the 3'-GST(TetR) primer; #1-5'-GST(TetR) can anneal to the 5' end of the resulting DNA fragment and extend the 5' end sequence.

The final PCR product contains the GST gene fused to the promoter region used to control TetR expression in pWH353 or pWH354, and it has an SpeI site at its 5' end and a BstEII site at its 3' end. The amplified DNA was purified with the Wizard PCR Preparation and Purification Kit (Promega) and cloned into the pT7Blue-3 vector (Novagen), resulting in a clone designated pT7Blue-3-GST. The cloned DNA fragment in pT7Blue-3-GST was then excised from the vector with restriction endonucleases SpeI and BstEII, gel purified, and cloned into the SpeI/BstEII sites of pWH353 and pWH354, resulting in plasmids pC$^3$876 and pC$^3$878, respectively. These two plasmids have the same sequence as pWH353 or pWH354, except that the GST open reading frame sequence has been substituted for the TetR open reading frame in the original plasmids.

E. pC$^3$874, pC$^3$875, and pC$^3$875 Derivatives

As the multilinker cloning site in pT7Blue-3 is flanked by two EcoRI sites, the cloned GST DNA fragment in pT7Blue-3-GST was also excised from pT7Blue-3-GST with EcoRI digestion. The agarose gel-purified DNA fragment was then ligated to the EcoRI vector portion of pC$^3$859 containing the origin of replication. The resulting plasmids pC$^3$874 and pC$^3$875 have the GST gene in alternative orientations.

The following DNA sequence, which encoded the JT01 peptide (DPNTWQLRWPMH; SEQ ID NO:17) followed by a Gly-Gly-Arg-Gly-Gly-Met (SEQ ID NO:18) linker, was inserted after the initiation ATG codon of the GST gene in pC$^3$875, resulting in plasmid pC$^3$882:

5'gatcctaatacatggcagttgaggtggcctatgcatggcggccgcggaggtatg (SEQ ID NO:19).

The following DNA sequence, which encoded JT01 peptide flanked by a Ser-Ser dipeptide on each side (ssJT01ss) and followed by a Gly-Gly-Arg-Gly-Gly-Met linker, was inserted after the initiation ATG codon of the GST gene in pC$^3$875, resulting in plasmid pC$^3$883:

5'agctctgatcctaatacatggcagt-tgaggtggcctatgcattcttcaggcggccgcggaggtatg (SEQ ID NO:20)

The following DNA sequence, which encoded a peptide with the sequence of Ser-Arg-Trp-Glu-Lys-Tyr-Ile-Asn-Ser-Phe-Glu-Leu-Asp-Ser-Arg-Gly-Gly-Arg-Gly-Gly-Met (LysN2), (SEQ ID NO. 21) was inserted after the initiation ATG codon of the GST gene in pC$^3$875, resulting in plasmid pC$^3$888:

5'tctagatgggaaaaatatattaat-tcttttgaattagattctcgaggtggtagaggtggaatg (SEQ ID NO:22)

The following DNA sequence, which encoded a peptide with the sequence of Ser-Ser-Gln-Gly-Thr-Met-Arg-Trp-Phe-Asp-Trp-Tyr-Arg-Ser-Arg-Gly-Gly-Arg-Gly-Gly-Met (LysN3), (SEQ ID NO.23) was inserted after the initiation ATG codon of the GST gene in pC$^3$875, resulting in plasmid pC$^3$889:

5'agctctcaaggtactatgagatg-gtttgattggtatagatctgaggtggtagaggtggaatg (SEQ ID NO:24)

F. pC$^3$884 and pC$^3$886

The green fluorescence protein (GFP) gene was amplified from plasmid pQBI63 (Quantum Biotechnologies Inc.) using the following oligonucleotides with Taq DNA polymerase:

5'GFP(NotI): 5'agcaccttggcggccgcggaggtgctag-caaaggagaagaactcttcac (SEQ ID NO:25)

3'GFP(BstEII): 5'aactgaggtaacctcagttgtacagtcatccatgcc (SEQ ID NO:26).

The amplified DNA was purified with the Wizard PCR Preparation and Purification Kit, and digested with restriction endonucleases NotI and BstEII. The digested DNA was gel purified and ligated to the NotI/BstEII sites of pC$^3$882, resulting in pC$^3$886.

The maltose binding protein (MBP) gene was amplified from plasmid pMAL-c2 (New England Biolabs) with Taq DNA polymerase using the following oligonucleotides:

5'MalE(NotI): 5'tttaccttggcggccgcggaggtaaact-gaagaaggtaaactggtaatctgg (SEQ ID NO:27);

3'MalE(BstEII): 5'acttagggtaaccttaagtctgc gcgtctttcagggcttc (SEQ ID NO:28)

The amplified DNA was purified with the Wizard PCR Preparation and Purification Kit, and digested with restriction endonucleases NotI and BstEII. The digested DNA was gel purified and ligated to the NotI/BstEII sites of pC$^3$882, resulting in pC$^3$884.

Example 3

Characterization of Expression Plasmids

A. pWH353 and pWH354 pWH353 and pWH354 were transformed separately into *S. aureus* RN4220 cells by electroporation. The transformants were tested for inducible expression by growing in LB broth containing 30 µg/ml kanamycin. After the OD$_{600}$ reached 0.5, the cultures were split and tetracycline was added to one set of the cultures to a final concentration of 0.5 µg/ml. The induction was for 3 hours at 37° C. The *S. aureus* cells were then pelleted and resuspended in 80 mM Tris-HCl, pH 7.4 containing 200 µg/ml lysostaphin, incubated at 37° C. for 5 minutes, frozen and thawed twice in a dry ice/ethanol bath and in a 37° C. water bath. The samples were then sonicated twice and centrifuged at 14,000 g for 10 minutes, and the supernatants were collected and subjected to analysis on a 4–20% acrylamide gradient gel, by SDS-PAGE. The CAT activities in these samples were determined and summarized in Table 1. The results indicated that CAT is inducibly expressed, although the expression levels are not high enough to produce a visible band by Coomassie staining on an SDS polyacrylamide gel.

TABLE

Inducible expression of chloramphenicol acetyltransferase activity in *S. aureus*

| Plasmid | Induction | Relative CAT Activity |
| --- | --- | --- |
| No Plasmid | − | ND |
| No Plasmid | + | ND |
| pWH353 |   | 41 |
| pWH353 | + | >4110 |
| pWH354 |   | 1 |
| pWH354 | + | 350 |

ND: Not detectable.

Expression of GST with pWH353-2G in *S. aureus* RN4220 was also characterized. The transformants of pWH353-2G were tested for inducible expression by growing in LB broth containing 30 µg/ml kanamycin. After OD$_{600}$ reached 0.5, the cultures were divided into 4 tubes and anhydrotetracycline was added to 0, 0.0625, 0.25, or 1 µg/ml. The induction was for 3 hours at 37° C. The *S. aureus* cells were then pelleted and resuspended in 1×PBS containing 100 µg/ml lysostaphin, incubated at 37° C. for 5 minutes, frozen and thawed twice on dry ice/ethanol and 37° C. water bath. The samples were then sonicated twice and centrifuged at 14,000 g for 10 minutes and the supernatants were collected and subjected to analysis on a 4–20% SDS-PAGE. The result indicated that GST expression level was very low, not detectable by Coomassie blue staining. Characterization of pWH354-2G, pWH353-2G-M1, and pWH354-2G-M1 transformants of RN4220 generated similar results.

B. Expression and Growth Characterization of *S. aureus* Cells Harboring pWH353(ΔtetR) and pWH354(ΔtetR), or pWH354-2G(ΔtetR)

pWH353(ΔtetR), pWH354(ΔtetR) and pWH354-2G (ΔtetR) were transformed into separate cultures of *S. aureus* CYL316t cells by electroporation. Overnight cultures of CYL316t/pWH353(ΔtetR), CYL316t/pWH354(ΔtetR) and CYL316t/pWH354-2G(ΔtetR) were diluted 100-fold in fresh LB with 5 µg/ml erythromycin and 25 µg/ml kanamycin. After the $OD_{600}$ reached 0.5, the cultures were split into two tubes, and anhydrotetracycline was added to one set of the cultures to a final concentration of 0.2 µg/ml. The induction was for 3 hours at 37° C. The *S. aureus* cells were then pelleted and resuspended in 1×PBS containing 100 µg/ml lysostaphin, incubated at 37° C. for 5 minutes, frozen and thawed twice in a dry ice/ethanol bath and in a 37° C. water bath. The samples were then sonicated twice and centrifuged at 14,000 g for 10 minutes. The supernatants were collected and subjected to analysis on a 4–20% acrylamide gradient gel, by SDS-PAGE. Cultures of CYL316t/pWH353(ΔtetR) were also tested, with similar results. The results indicated that removing the tetR gene from the pWH353 and pWH354 plasmids drastically increased efficiency of CAT expression, to the point where a protein band became visible by Coomassie blue staining on an SDS-polyacrylamide gel, while GST expression was not significantly enhanced.

Growth of CYL316t, CYL316t/pWH353(ΔtetR), CYL316t/pWR354(ΔtetR) and CYL316t/pWH354-2G (ΔtetR) was also characterized by the following experiment. Overnight cultures of CYL316t, CYL316t/pWH353(ΔtetR), CYL316t/pWH354(ΔtetR) and CYL316t/pWH354-2G (ΔtetR) were diluted 100-fold in fresh tryptone-soy broth (TSB; Difco) containing 5 µg/ml erythromycin and 25 µg/ml kanamycin (for CYL316t/pWH353(ΔtetR), CYL316t/pWH354(ΔtetR) and CYL316t/pWH354-2G(ΔtetR)). After growing for 1 hour at 37° C., each culture was split into two tubes and to one anhydrotetracycline was added to 200 ng/ml. The $OD_{600}$'s of the cultures were then recorded at various time points. The results depicted in FIGS. 3A–3D demonstrate that anhydrotetracycline induction caused a significant inhibition in *S. aureus* growth.

C. Growth Characterization of *S. aureus* Cells Carrying pC$^3$859

Figure 3A:
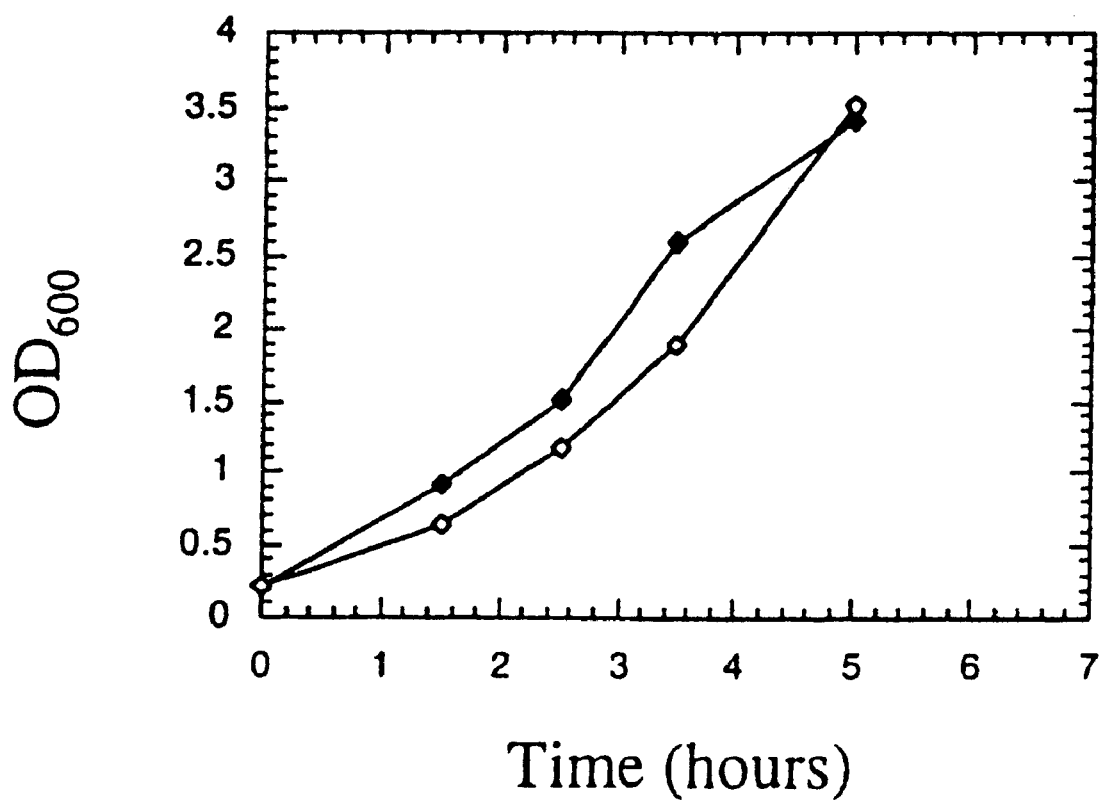
FIG. 3A is a graph showing the growth, as measured by $OD_{600}$, of *S. aureus* strain CYL316t in the presence (open diamonds) or absence (filled diamonds) of 200 ng/ml of anhydrotetracycline.
Figure 3B:
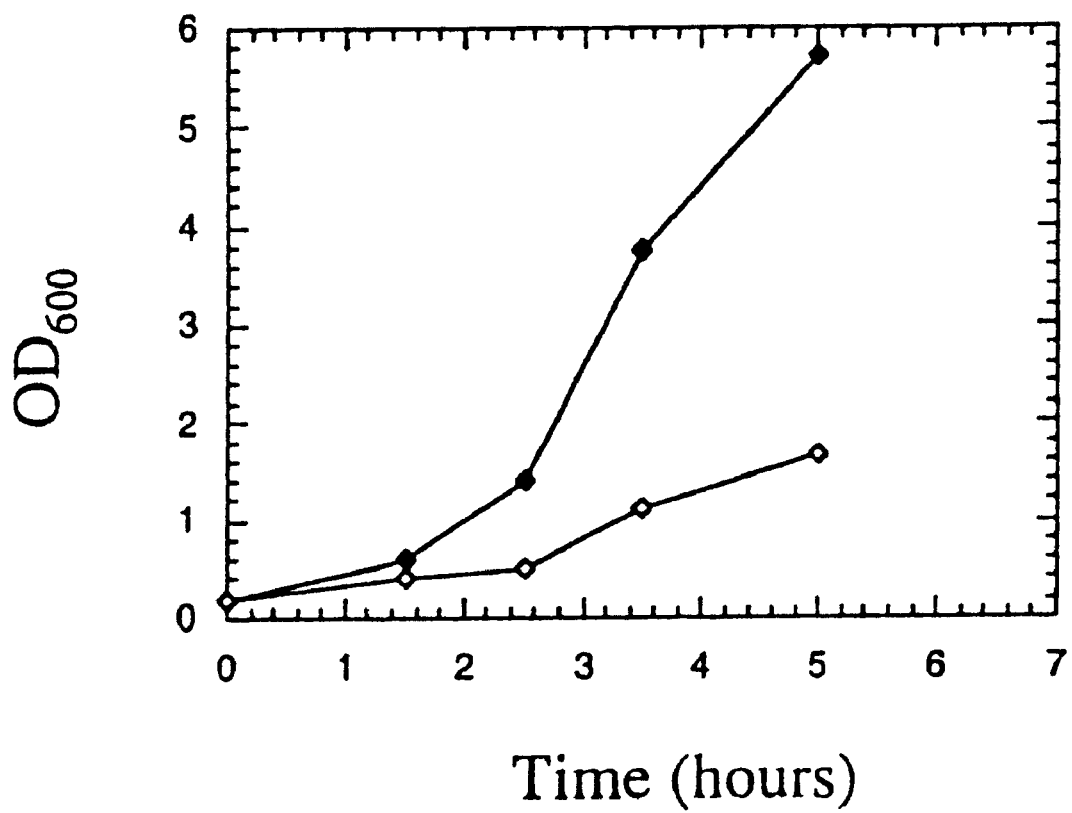
FIG. 3B is a graph showing the growth, as measured by $OD_{600}$, of *S. aureus* strain CYL316t/pWH353(ΔtetR) in the presence (open diamonds) or absence (filled diamonds) of 200 ng/ml of anhydrotetracycline.
Figure 3C:
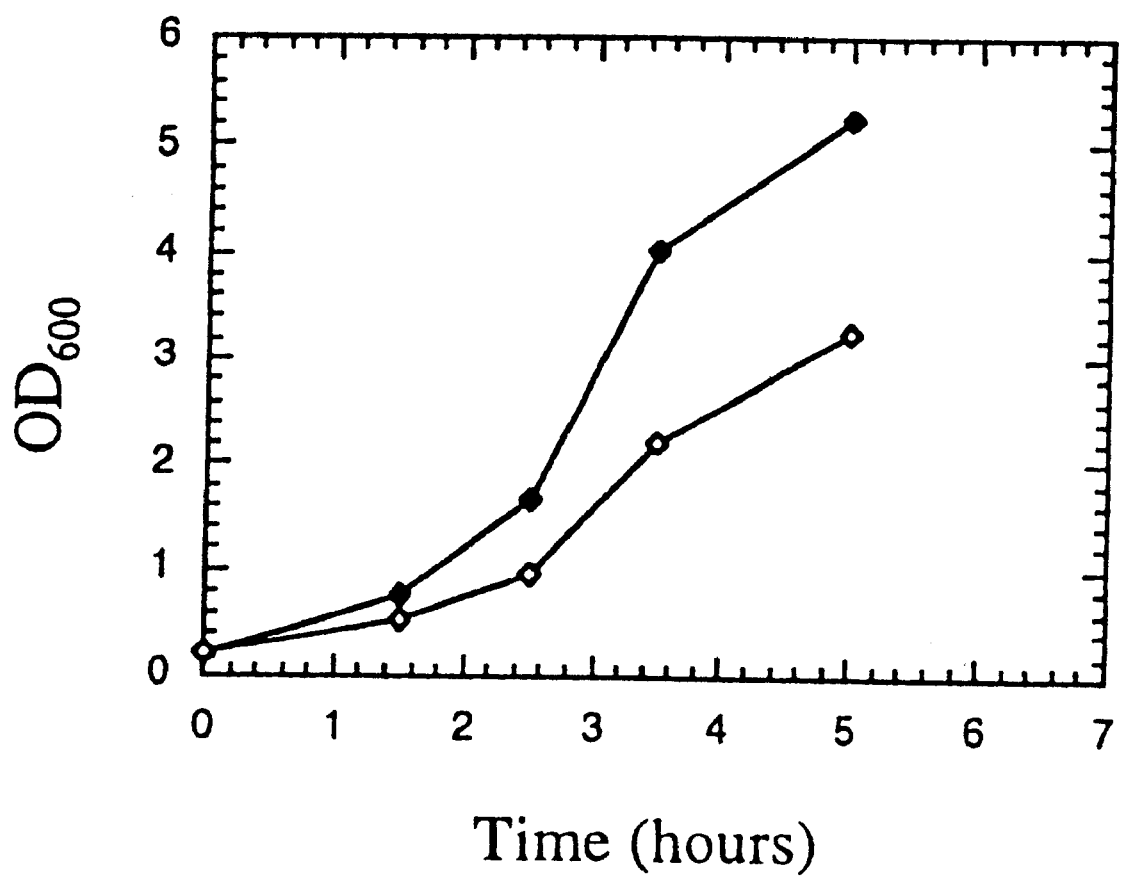
FIG. 3C is a graph showing the growth, as measured by $OD_{600}$, of *S. aureus* strain CYL316t/pWH354(ΔtetR) in the presence (open diamonds) or absence (filled diamonds) of 200 ng/ml of anhydrotetracycline.
Figure 3D:
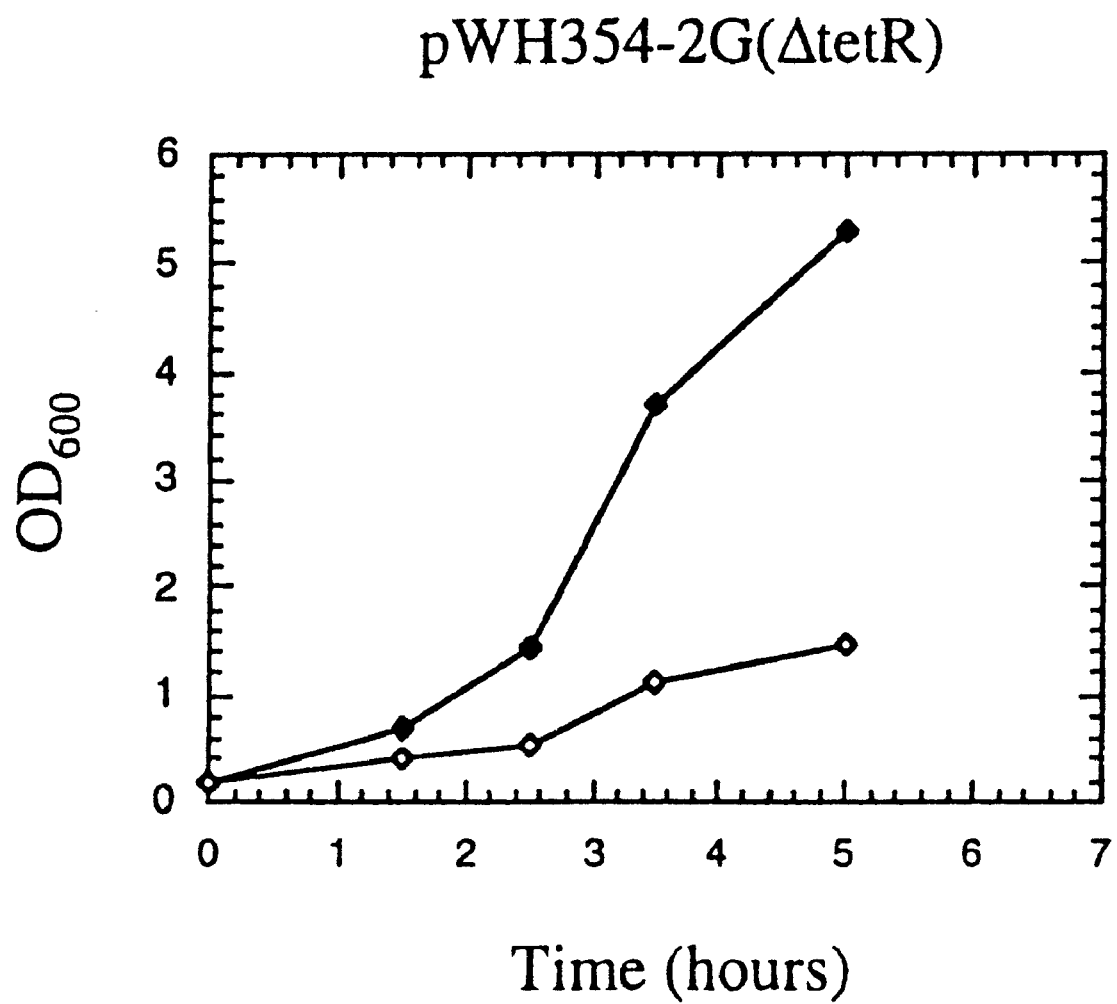
FIG. 3D is a graph showing the growth, as measured by $OD_{600}$, of *S. aureus* strain CYL316t/pWH354-2G(ΔtetR) in the presence (open diamonds) or absence (filled diamonds) of 200 ng/ml of anhydrotetracycline.
Figure 3E:
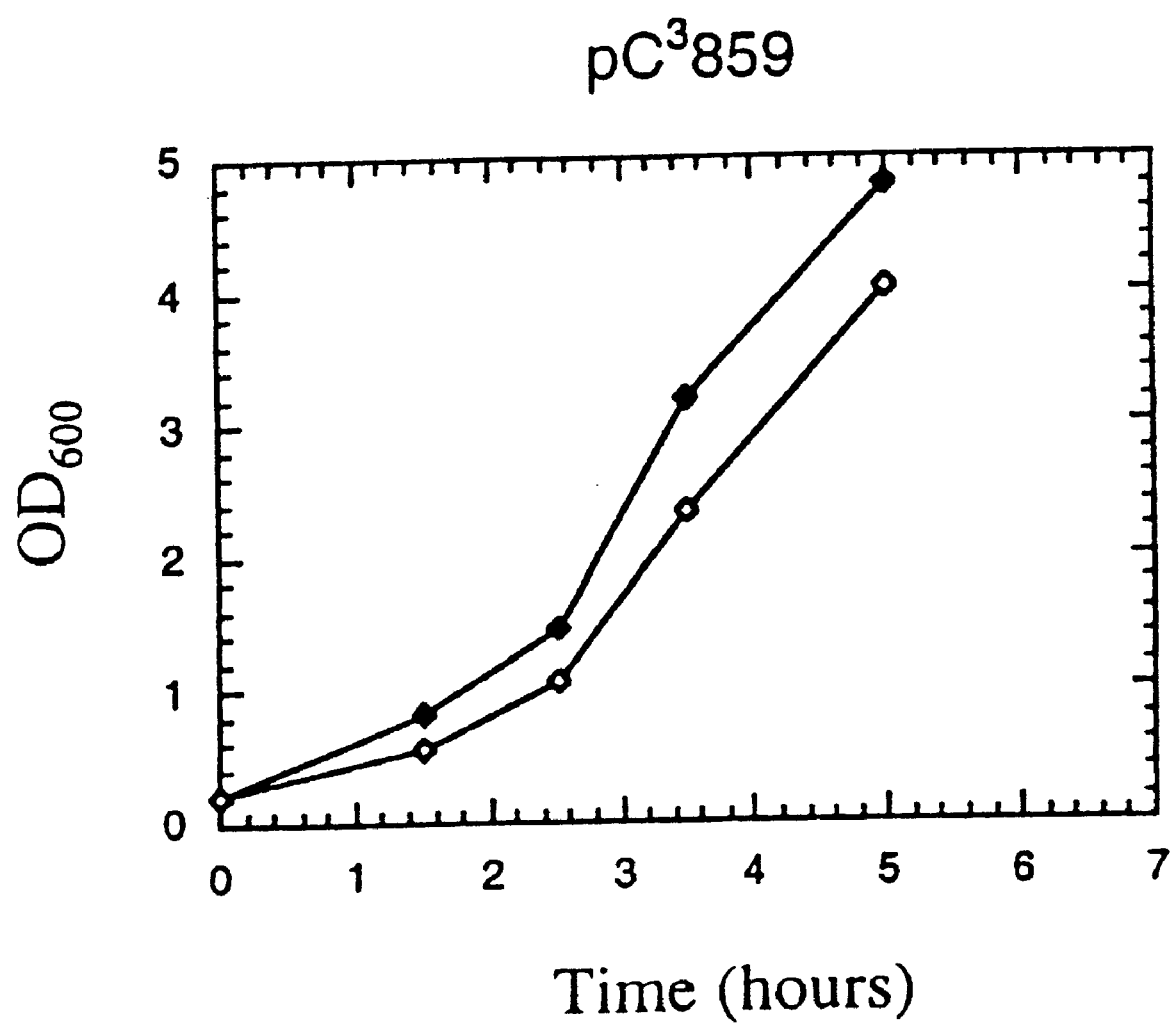
FIG. 3E is a graph showing the growth, as measured by $OD_{600}$, of *S. aureus* strain CYL316t/$pC^3859$ in the presence (open diamonds) or absence (filled diamonds) of 200 ng/ml of anhydrotetracycline.

An overnight culture of CYL316t/pC$^3$859 was diluted 100-fold in fresh TSB with 5 µg/ml erythromycin and 25 µg/ml kanamycin. After growing for 1 hour at 37° C., the culture was split into two tubes. To one, anhydrotetracycline was added to 200 ng/ml. The $OD_{600}$ of the culture was then recorded at various time points. The result is depicted in FIG. 3E, which demonstrates that the anhydrotetracycline induction related cytotoxicity observed with *S. aureus* cells carrying pWH353(ΔtetR) or pWH354(ΔtetR) is much reduced for *S. aureus* cells harboring pC$^3$859, by comparison.

D. Expression Characterization of *E. coli* or *S. aureus* Cells Harboring pC$^3$859 or Its Derivatives Plasmids pC$^3$859, pC$^3$859-GST, pC$^3$859-GFP, and pC$^3$859-MBP were each transformed into separate cultures of *E. coli* DH5αPRO and *S. aureus* CYL316t. Overnight cultures of the resulting *E. coli* or *S. aureus* transformant cells were diluted 100-fold in fresh LB with 50 µg/ml spectinomycin and 25 µg/ml kanamycin for *E. coli* cells or LB with 5 µg/ml erythromycin and 25 µg/ml kanamycin for *S. aureus* cells. After the $OD_{600}$ reached 0.5, the cultures were split into two tubes, and anhydrotetracycline was added to one set of the cultures to 0.2 µg/ml. The induction was for 3 hours at 37° C. The *E. coli* cells were pelleted and boiled 5 minutes in SDS-PAGE sample buffer. The *S. aureus* cells were pelleted and resuspended in 1×PBS containing 100 µg/ml lysostaphin, incubated at 37° C. for 5 minutes, frozen and thawed twice in a dry ice/ethanol bath and in a 37° C. water bath. The samples were then sonicated twice and centrifuged at 14,000 g for 10 minutes and the supernatants were mixed with SDS-PAGE sample buffer and boiled for 5 minutes. The samples were subjected to analysis on a 4–20% acrylamide gradient gel, by SDS-PAGE. The results indicated that while CAT can be efficiently expressed from pC$^3$859 in *S. aureus*, other genes, such as GST, GFP, or MBP are not efficiently expressed using the same genetic background.

E. Expression Characterization of *S. aureus* Cells Harboring pC$^3$876, pC$^3$878, pC$^3$874, or pC$^3$875

Plasmids pC$^3$876, pC$^3$878, pC$^3$874, and pC$^3$875 were transformed into separate cultures of *S. aureus* CYL316t. Overnight cultures of the resulting *S. aureus* cells were diluted 100-fold in fresh LB with 5 µg/ml erythromycin and 25 µg/ml kanamycin for *S. aureus* cells. After the $OD_{600}$ reached 0.5, the cultures were split into two tubes and anhydrotetracycline was added to one set of the cultures to 0.2 µg/ml. The induction was for 3 hours at 37° C. The *S. aureus* cells were pelleted and resuspended in 80 mM Tris-HCl, pH 7.4 containing 200 µg/ml lysostaphin, incubated at 37° C. for 5 minutes, frozen and thawed twice in a dry ice/ethanol bath and in a 37° C. water bath. The samples were then sonicated twice and centrifuged at 14,000 g for 10 minutes and the supernatants were mixed with SDS-PAGE sample buffer and boiled for 5 minutes. The samples were subjected to analysis on a 4–20% acrylamide gradient gel, by SDS-PAGE. The results indicated that GST gene can be efficiently expressed with these constructs. GST from the above cell lysates was also purified with glutathione-Sepharose, and analyzed by SDS-PAGE. The results indicated that pC$^3$875 had the lowest level of basal expression from the tet promoter/operator.

F. Expression Characterization of pC$^3$882 and pC$^3$883 in CYL316t

Plasmid pC$^3$882 and pC$^3$883 were transformed into separate cultures of *S. aureus* CYL316t. Overnight cultures of the resulting *S. aureus* transformant cells were diluted 100-fold in fresh LB with 5 µg/ml erythromycin and 25 µg/ml kanamycin. After the $OD_{600}$ reached 0.5, the cultures were split into two tubes and anhydrotetracycline was added to one set of the cultures to 0.2 µg/ml. The induction was for 3 hours at 37° C. The *S. aureus* cells were pelleted and resuspended in 1×PBS containing 100 µg/ml lysostaphin, incubated at 37° C. for 5 minutes, and frozen and thawed twice in a dry ice/ethanol bath and in a 37° C. water bath. The samples were then sonicated twice and centrifuged at 14,000 g for 10 minutes, and the supernatants were mixed with SDS-PAGE sample buffer and boiled for 5 minutes. The samples were subjected to analysis on a 4–20% acrylamide gradient gel, by SDS-PAGE. The results indicated that both JT01-GST and ssJT01ss could be efficiently expressed, and the expression for JT01-GST was significantly higher than ssJT01ss-GST. With an ELISA assay (Pharmacia; product #27-4592), it was determined that expression of JT01-GST increased about 1000-fold upon anhydrotetracycline induction.

JT01-GST and ssJT01ss-GST fusion polypeptides were also purified from the above described cell extracts using glutathione affinity resin. The purified peptide-GST fusion polypeptides were tested for their inhibitory activity on *S. aureus* MetRS with 2 mM ATP, 50 μM methionine, and 90 μM *E. coli* total tRNA as the substrates. Under these conditions, JT101-GST only inhibited 60% of *S. aureus* activity with an $IC_{50}$ (peptide concentration required to inhibit 50% MetRS activity) about 15 nM, while both free JT101 peptide and ssJT01ss-GST could fully inhibit *S. aureus* MetRS activity with an $IC_{50}$ of about 100 nM.

Figure 5A:
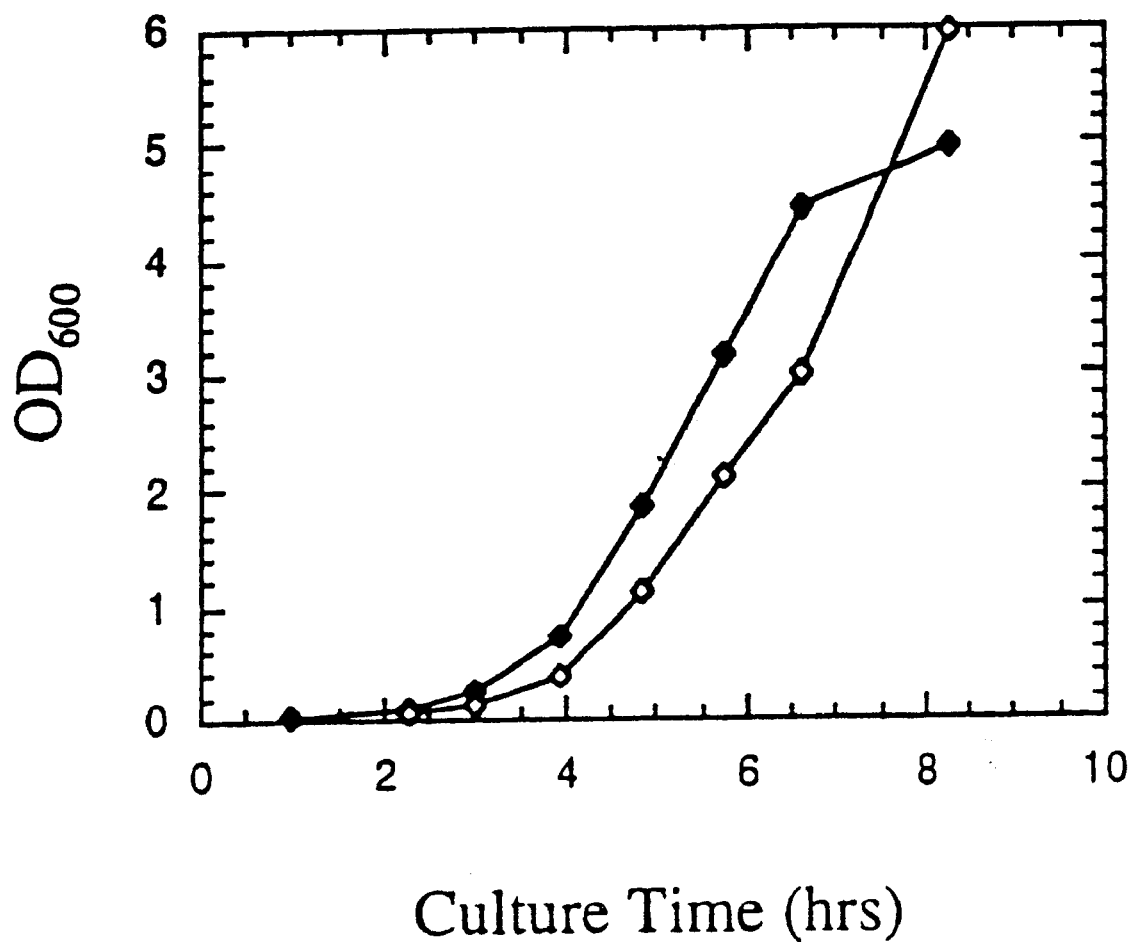
FIG. 5A is a graph showing the growth, as measured by $OD_{600}$, of *S. aureus* strain CYL316tt bearing $pC^3875$ upon induction (filled diamonds) or no induction (open diamonds) of gene expression under control of the tetracycline promoter/operator.
Figure 5B:
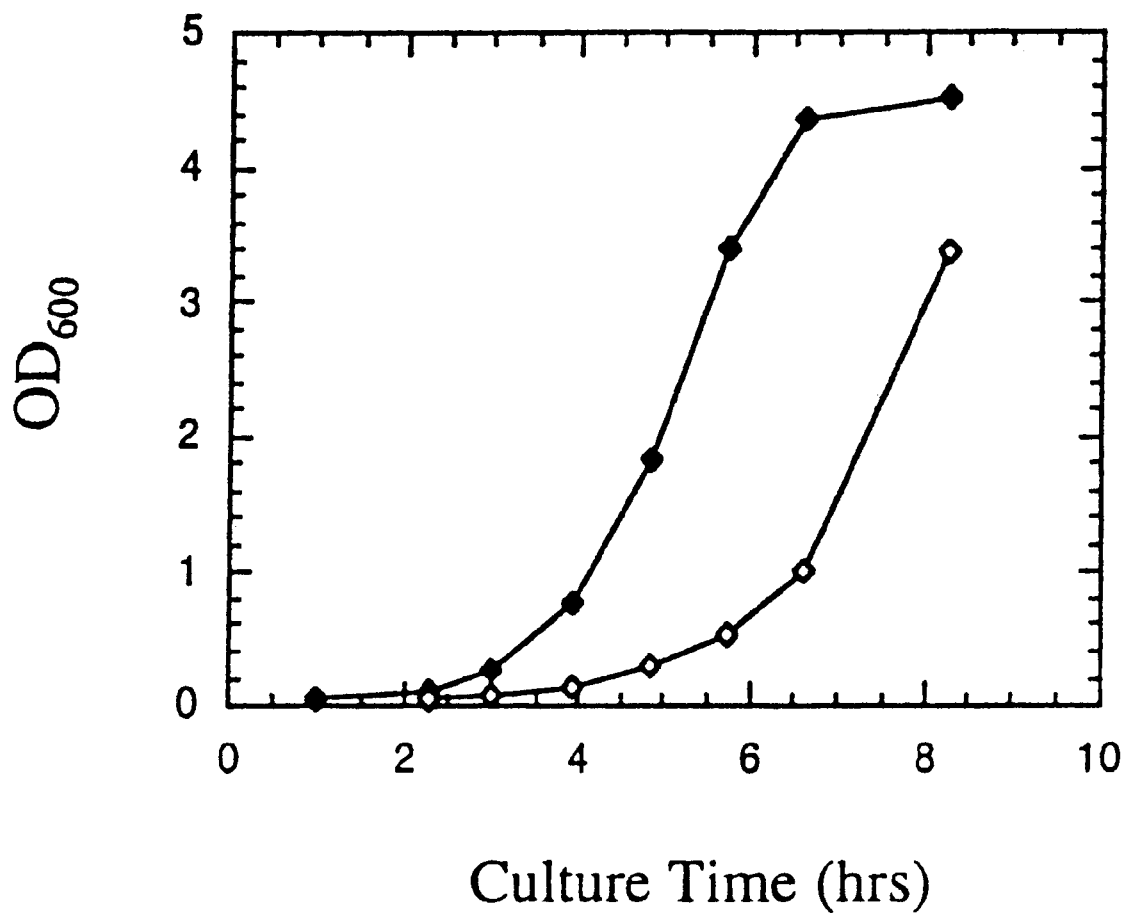
FIG. 5B is a graph showing the growth, as measured by $OD_{600}$, of *S. aureus* strain CYL316tt bearing $pC^3882$ upon induction (filled diamonds) or no induction (open diamonds) of gene expression under control of the tetracycline promoter/operator.
Figure 5C:
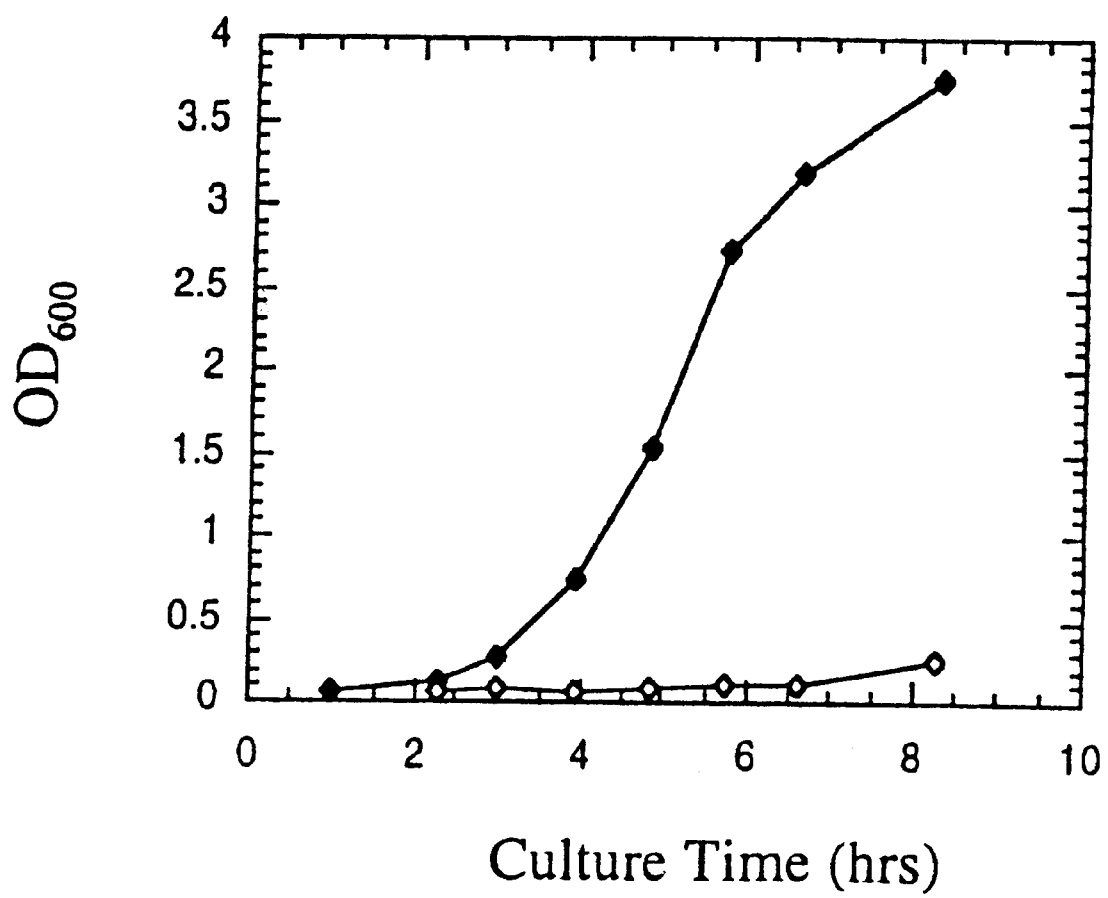
FIG. 5C is a graph showing the growth, as measured by $OD_{600}$, of *S. aureus* strain CYL316tt bearing $pC^3883$ upon induction (filled diamonds) or no induction (open diamonds) of gene expression under control of the tetracycline promoter/operator.

G. Growth Characterization of *S. aureus* cells Carrying Plasmid $pC^3882$ or $pC^3883$ Plasmids $pC^3882$ and $pC^3883$ were transformed separately into *S. aureus* strains CYL316t and CYL316tt. Overnight cultures of the resulting *S. aureus* transformant cells grown in TSB with 5 μg/ml erythromycin and 25 μg/ml kanamycin were diluted 100-fold in fresh TSB with 5 μg/ml erythromycin and 25 μg/ml kanamycin. After growing for 1 hour at 37° C., the culture was split into two tubes and to one, anhydrotetracycline (for CYL316t strains) or tetracycline (for CYL316tt strains) was added to 200 ng/ml and 1 μg/ml, respectively. The $OD_{600}$ of the culture was then recorded at various time points. The results depicted in FIGS. 5A, 5B, and 5C demonstrate that induction of expression of JT01-GST or ssJT01ss-GST, but not GST alone, caused significant inhibition of *S. aureus* growth. Between the two fusion polypeptides, ssJT01ss-GST expression had the stronger growth inhibitory effect.

H. Expression of JT01-GFP, JT01-MBP Fusions

Plasmid $pC^3884$ and $pC^3886$ were each transformed separately into separate cultures of *S. aureus* CYL316tt. Overnight cultures of the resulting transformant *S. aureus* cells were diluted 100-fold in fresh LB with 5 μg/ml erythromycin and 25 μg/ml kanamycin. After the $OD_{600}$ reached 0.5, the cultures were split into two tubes and tetracycline was added to one set of the cultures to 1 μg/ml. The induction was for 3 hours at 37° C. The *S. aureus* cells were pelleted and resuspended in 1×PBS containing 100 μg/ml lysostaphin, incubated at 37° C. for 5 minutes, frozen and thawed twice in a dry ice/ethanol bath and in a 37° C. water bath. The samples were then sonicated twice and centrifuged at 14,000g for 10 minutes and the supernatants were mixed with SDS-PAGE sample buffer and boiled for 5 minutes. Analysis of the resulting samples on a SDS-polyacrylamide gel revealed that both JT01-GFP and JT01-MBP polypeptides were efficiently expressed.

I. Expression of LysN2-GST, and LysN3-GST Fusions

Plasmid $pC^3888$ or $pC^3889$ was transformed into *S. aureus* CYL316t. Overnight cultures of the resulting *S. aureus* cells were diluted 100-fold in fresh LB with 5 μg/ml erythromycin and 25 μg/ml kanamycin. After the $OD_{600}$ reached 0.5, the cultures were split into two tubes and anhydrotetracycline was added to one set of the cultures to 0.2 μg/ml. The induction was for 3 hours at 37° C. The *S. aureus* cells were pelleted and resuspended in 1×PBS containing 100 μg/ml lysostaphin, incubated at 37° C. for 5 minutes, frozen and thawed twice in a dry ice/ethanol bath and in a 37° C. water bath. The samples were then sonicated twice and centrifuged at 14,000 g for 10 minutes, and the supernatants were mixed with SDS-PAGE sample buffer and boiled for 5 minutes. Examination of the resulting samples on a SDS-polyacrylamide gel revealed that both LysN2-GST and LysN3-GST were efficiently expressed.

Example 4

Protection of a Lethal *S. aureus* Infection by Intracellular Expression of a Peptide In Vivo In experiments using *S. aureus* cells grown in culture, intracellularly expressed ssJT01ss bound to and inhibited a specific essential cellular target in a manner similar to that of an antimicrobial drug. Hence induction of expression of this peptide during an infection should have the effect of an antibiotic. An established animal infection model was used to test this concept (Onyegji, C. O. et al., *Antimicrobial Agents and Chemotherapy* 38:112–117, 1994).

Six groups of CD-1 female mice (5 mice per group, Charles River Laboratories, Wilmington, Ma.) weighing 20–24 grams were used in this experiment. The inoculum was prepared from $CYL316tt/pC^3883$ (encoding a ssJT01ss peptide-GST fusion protein under the control of the tet operon) which was cultured at 37° C. for 17 hours in TS broth containing erythromycin and kanamycin. $1.6×10^{10}$ cfu (colony-forming units) of *S. aureus* $CYL316tt/pC^3883$ ($OD_{600}$ of $0.1=10^8$ cfu/ml) from the overnight culture were diluted to 20 ml with 0.01 M PBS (Sigma P-0261) containing 8% hog gastric mucin (Sigma M-2378) as well as 50 μg/ml kanamycin and 10 μg/ml erythromycin. Each mouse of groups 1 through 4 was injected with 0.5 ml of the inoculum intraperitoneally (i.p.), equivalent to $4×10^8$ cfu/mouse (lethal dose). Groups 5 and 6 served as vector controls. Each mouse of these two groups was injected with $4×10^8$ cfu of $CYL316tt/pC^3875$, which was cultured and processed the same way as $CYL316tt/pC^3883$. One half hour and four hours after the inoculation, groups 1 and 5 received a saline injection i.p. at 10 ml/kg; groups 2 and 6 received i.p. injections of tetracycline (Sigma T-3383) at 8 mg/kg; group 3 received i.p. injections of tetracycline at 4 mg/kg; group 4 received i.p. injections of ciprofloxacin (Bayer 851510, dissolved in water) at 50 mg/kg. The injection volume for all the animals was 10 ml/kg. Surviving mice were counted at 7 days post inoculation. Ciprofloxacin given at 50 mg/kg protected all infected animals from lethal infection.

The data summarized in Table 2 demonstrate that induction of intracellular expression of the ssJT01ss peptide can be achieved in an animal infection. Inhibition of *S. aureus* MetRS by the intracellularly expressed ssJT01ss peptide cured a lethal infection in a mouse model.

TABLE 2

Inhibition of *S. aureus* growth in mice by intracellular production of *S. aureus* MetRS inhibitor

| Experimental Condition | # of Mice Tested | # of Mice Survival |
|---|---|---|
| M1 Peptide | | |
| Saline, 10 mg/kg C2 | 5 | 0 |
| Inducer, mg/kg C2 | 5 | 5 |
| Expression Control | | |
| Saline, 10 mg/kg C2 | 5 | 0 |
| Inducer, mg/kg C2 | 5 | 0 |

The relevant teachings of all references cited herein are hereby incorporated by reference herein in their entirety.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A nucleic acid replicon that replicates in *Staphylococcus aureus*, said replicon comprising a tetracycline-inducible promoter/operator region, wherein the promoter of said promoter/operator region does not control production of tet repressor or chloramphenicol acetyltransferase, and further comprising a linker site downstream of the promoter/operator region such that insertion, in frame, of a nucleic acid segment encoding a gene product results in a derivative replicon in which production of the gene product in the bacteria is under tetracycline-inducible control by the tetracycline-inducible promoter/operator region in said replicon.

2. The replicon of claim 1 which is a plasmid.

3. The replicon of claim 1 wherein the gene product is a polypeptide.

4. A bacterial cell harboring the replicon of claim 1.

5. A nucleic acid replicon that replicates in *Staphylococcus aureus*, said replicon comprising a tetracycline-inducible promoter/operator region and a linker site downstream of the promoter/operator, wherein the linker is within or adjacent to a nucleic acid segment encoding a carrier polypeptide, such that insertion, in frame, of a nucleic acid encoding a second polypeptide results in a derivative replicon, which when introduced into said bacteria, inducibly produces a fusion polypeptide.

6. The replicon of claim 5 which is a plasmid.

7. A bacterial cell harboring the replicon of claim 5.

8. The replicon of claim 5 wherein the carrier polypeptide is a glutathione S-transferase or a portion thereof.

9. The replicon of claim 5 wherein the carrier polypeptide is a maltose binding protein.

10. The replicon of claim 5 wherein the carrier polypeptide is a green fluorescence protein.

11. A replicon comprising $P_{JT}$/TetO.

12. The replicon of claim 11 further comprising an open reading frame under tetracycline-inducible regulation by $P_{JT}$/TetO.

13. The replicon of claim 11 which replicates in one or more species of Gram-positive bacteria.

14. The replicon of claim 11 which replicates in one or more species of staphylococci.

15. A replicon comprising $P_{JT}$/TetO and an open reading frame, under tetracycline-inducible regulation by $P_{JT}$/TetO, encoding a fusion protein.

16. A replicon comprising $P_{JT}$/TetO and an open reading frame, under tetracycline-inducible regulation by $P_{JT}$/TetO, encoding a glutathione S-transferase fusion protein comprising glutathione S-transferase or portion thereof sufficient for affinity purification of the fusion protein on glutathione affinity medium.

17. A replicon comprising $P_{JT}$/TetO and an open reading frame, under tetracycline-inducible regulation by $P_{JT}$/TetO, encoding a maltose binding fusion protein comprising maltose binding protein or a portion thereof sufficient for affinity purification of the fusion protein on affinity medium.

18. A replicon comprising $P_{JT}$/TetO and an open reading frame, under tetracycline-inducible regulation by $P_{JT}$/TetO, encoding a green fluorescence fusion protein comprising green fluorescence protein or a portion thereof.

19. The plasmid pCL84t.

20. The plasmid pCL84tt.

21. The plasmid pC³874.

22. The plasmid pC³875.

23. A Gram-positive bacterium comprising a tetracycline repressor gene, a gene conferring tetracycline resistance, and a plasmid, said plasmid comprising a gene encoding a fusion polypeptide under control of a tetracycline-inducible promoter/operator region.

24. The bacterium of claim 23, wherein the Gram-positive bacterium is *Staphylococcus aureus*.

25. A system for inducible production of a gene product, said system comprising *Staphylococcus aureus* bacterial cells comprising:
   a) a nucleic acid replicon that replicates in *Staphylococcus aureus* bacteria, said replicon comprising a tetracycline-inducible promoter/operator region, wherein the promoter of said promoter/operator region does not control production of tet repressor or chloramphenicol acetyltransferase, and further comprising an open reading frame encoding the gene product under tetracycline-inducible control by the tetracycline-inducible promoter/operator region in said replicon;
   b) one or more genes producing a tetracycline resistant phenotype; and
   c) one or more genes expressing a repressor of the tetracycline-inducible promoter/operator.

26. A system for inducible production of a fusion polypeptide, said system comprising *Staphylococcus aureus* bacterial cells comprising:
   a) a nucleic acid replicon that replicates in *Staphylococcus aureus*, said replicon comprising a tetracycline-inducible promoter/operator region and a gene encoding a fusion polypeptide under control of said promoter/operator region;
   b) one or more genes producing a tetracycline resistant phenotype; and
   c) one or more genes expressing a repressor of the tetracycline-inducible promoter/operator.

27. A system for inducible production of a gene product, said system comprising bacterial cells comprising:
   a) a replicon comprising $P_{JT}$/TetO and an open reading frame encoding the gene product under tetracycline-inducible regulation by $P_{JT}$/TetO;
   b) one or more genes producing a tetracycline resistant phenotype; and
   c) one or more genes a expressing repressor of the tetracycline-inducible promoter/operator.

28. The system of claim 27 wherein the bacterial cells are *Staphylococcus aureus*.

29. The system of claim 27 wherein production of a fusion polypeptide is inducible by tetracycline to at least about 10 times the uninduced level.

30. The system of claim 27 wherein the tetracycline resistant phenotype is produced by Tet(M).

31. The system of claim 27 wherein the gene product is an enzyme inhibitor.

* * * * *